US012644143B2

(12) United States Patent
Cheng et al.

(10) Patent No.: US 12,644,143 B2
(45) Date of Patent: Jun. 2, 2026

(54) METHOD FOR THE DETERMINATION OF ANTIBIOTIC SUSCEPTIBILITY THROUGH STIMULATED RAMAN METABOLIC IMAGING

(71) Applicant: Purdue Research Foundation, West Lafayette, IN (US)

(72) Inventors: Ji-xin Cheng, West Lafayette, IN (US); Mohamed Seleem, West Lafayette, IN (US); Weili Hong, West Lafayette, IN (US)

( * ) Notice: Subject to any disclaimer, the term of this patent is extended or adjusted under 35 U.S.C. 154(b) by 1147 days.

(21) Appl. No.: 17/548,483

(22) Filed: Dec. 10, 2021

(65) Prior Publication Data

US 2023/0183773 A1 Jun. 15, 2023

Related U.S. Application Data

(63) Continuation of application No. 16/645,521, filed as application No. PCT/US2018/050241 on Sep. 10, 2018, now Pat. No. 11,231,371.

(60) Provisional application No. 62/556,013, filed on Sep. 8, 2017.

(51) Int. Cl.
*C12Q 1/18* (2006.01)
*G01N 21/65* (2006.01)

(52) U.S. Cl.
CPC .............. *C12Q 1/18* (2013.01); *G01N 21/65* (2013.01); *G01N 2201/06113* (2013.01)

(58) Field of Classification Search
CPC . C12Q 1/18; G01N 21/65; G01N 2201/06113
See application file for complete search history.

(56) References Cited

U.S. PATENT DOCUMENTS

| | | | |
|---|---|---|---|
| 5,991,653 A | 11/1999 | Richards-Kortum | |
| 7,869,031 B2 | 1/2011 | Lewis | |
| 7,889,334 B2 | 2/2011 | Krause | |
| 8,071,319 B2 | 12/2011 | Metzger | |
| 8,129,676 B2 | 3/2012 | Vestel | |
| 9,677,109 B2 | 6/2017 | Shamsheyeva | |
| 11,231,371 B2* | 1/2022 | Cheng ................... | G01N 21/65 |
| 2008/0059135 A1* | 3/2008 | Murugkar ............. | G01J 3/4338 703/11 |

(Continued)

FOREIGN PATENT DOCUMENTS

| | | |
|---|---|---|
| EP | 2981830 A1 | 2/2016 |
| WO | 2017089727 A1 | 6/2017 |

OTHER PUBLICATIONS

Liu, B. et al. Label-free spectroscopic detection of membrane potential using stimulated Raman scattering. Applied Physics Letters 106, 173704 (2015).

(Continued)

*Primary Examiner* — Jonathan M Hurst
(74) *Attorney, Agent, or Firm* — Gutwein Law; Tyler B. Droste

(57) ABSTRACT

A method for the determination of antibiotic susceptibility through stimulated Raman scattering microscopy is disclosed. The method utilizes a imaging apparatus adapted to collect a laser signal through a sample having a bacteria for imaging the metabolism of the sample. The sample can be manipulated with an antibiotic for imaging to determine the susceptibility of a bacteria to the provided antibiotic.

17 Claims, 27 Drawing Sheets

(56)                    References Cited

U.S. PATENT DOCUMENTS

| | | | |
|---|---|---|---|
| 2010/0136609 A1 | 6/2010 | Clay | |
| 2014/0087368 A1 | 3/2014 | Walsh | |
| 2016/0177366 A1 | 6/2016 | Auner | |
| 2020/0278301 A1* | 9/2020 | Cheng | C12Q 1/18 |
| 2021/0239618 A1* | 8/2021 | Cheng | G01N 21/65 |

OTHER PUBLICATIONS

Hong, W. et al. In situ Detection of a Single Bacterium in Complex Environment by Hyperspectral CARS Imaging. ChemistrySelect 1, 513-517 (2016).

O'Neill, J. Tackling drug-resistant infections globally: final report and recommendations; The review on antimicrobial resistance, 2016.

Sugden, R.; Kelly, R.; Davies, S. Nature microbiology 2016, 1, 16187.

Kumar, A.; Roberts, D.; Wood, K. E.; Light, B.; Parrillo, J. E.; Sharma, S.; Suppes, R.; Feinstein, D.; Zanotti, S.; Taiberg, L. Critical care medicine 2006, 34, 1589-1596.

Schoepp, N. G.; Schlappi, T. S.; Curtis, M. S.; Butkovich, S. S.; Miller, S.; Humphries, R. M.; Ismagilov, R. F. Science Translational Medicine 2017, 9, eaal3693.

Murray, C.; Adeyiga, O.; Owsley, K.; Di Carlo, D. Lab on a Chip 2015, 15, 1226-1229.

Hou, Z.; An, Y.; Hjort, K.; Sandegren, L.; Wu, Z. Lab on a Chip 2014, 14, 3409-3418.

Choi, J.; Jung, Y.- G.; Kim, J.; Kim, S.; Jung, Y.; Na, H.; Kwon, S. Lab on a Chip 2013, 13, 280-287.

Lu, Y.; Gao, J.; Zhang, D. D.; Gau, V.; Liao, J. C.; Wong, P. K. Analytical Chemistry 2013, 85, 3971-3976.

Kim, S. C.; Cestellosblanco, S.; Inoue, K.; Zare, R. N. Antibiotics 2015, 4, 455-466.

Choi, J.; Yoo, J.; Lee, M.; Kim, E.-G.; Lee, J. S.; Lee, S.; Joo, S.; Song, S. H.; Kim, E.-C.; Lee, J. C. Science translational medicine 2014, 6, 267ra174-267ra174.

Baltekin, Ö.; Boucharin, A.; Tano, E.; Andersson, D. I.; Elf, J. Proceedings of the National Academy of Sciences 2017, 114, 9170-9175.

Fredborg, M.; Andersen, K. R.; Jørgensen, E.; Droce, A.; Olesen, T.; Jensen, B. B.; Rosenvinge, F. S.; Sondergaard, T. E. Journal of Clinical Microbiology 2013, 51, 2047-2053.

Schoepp, N. G.; Khorosheva, E. M.; Schlappi, T. S.; Curtis, M. S.; Humphries, R. M.; Hindler, J. A.; Ismagilov, R. F. Angewandte Chemie International Edition 2016, 55, 9557-9561.

Barczak, A. K.; Hung, D. T. Proceedings of the National Academy of Sciences 2012, 109, 6217-6222.

Schröder, U.-C.; Beleites, C.; Assmann, C.; Glaser, U.; Hübner, U.; Pfister, W.; Fritzsche, W.; Popp, J.; Neugebauer, U. Scientific reports 2015, 5, 8217.

Tao, Y.; Wang, Y.; Huang, S.; Zhu, P.; Huang, W. E.; Ling, J.; Xu, J. Analytical Chemistry 2017, 89, 4108-4115.

Syal, K.; Mo, M.; Yu, H.; Iriya, R.; Jing, W.; Sui, G.; Wang, S.; Grys, T. E.; Haydel, S. E.; Tao, N. Theranostics 2017, 7, 1795-1805.

Hong, W.; Karanja, C. W.; Abutaleb, N. S.; Younis, W.; Zhang, X.; Seleem, M. N.; Cheng, J.-X. Analytical Chemistry 2018, 90, 3737-3743.

Berry, D.; Mader, E.; Lee, T. K.; Woebken, D.; Wang, Y.; Zhu, D.; Palatinszky, M.; Schintlmeister, A.; Schmid, M. C.; Hanson, B. T. Proceedings of the National Academy of Sciences 2015, 112, E194-E203.

Fu, D.; Yu, Y.; Folick, A.; Currie, E.; Farese Jr, R. V.; Tsai, T.-H.; Xie, X. S.; Wang, M. C. Journal of the American Chemical Society 2014, 136, 8820-8828.

Freudiger, C. W.; Min, W.; Saar, B. G.; Lu, S.; Holtom, G. R.; He, C.; Tsai, J. C.; Kang, J. X.; Xie, X. S. Science 2008, 322, 1857-1861.

Cheng, J.-X.; Xie, X. S. Science 2015, 350, aaa8870.

Zhang, C.; Zhang, D.; Cheng, J.-X. Annual review of biomedical engineering 2015, 17, 415-445.

Nanakumar, P.; Kovalev, A.; Volkmer, A. New Journal of Physics 2009, 11, 033026.

Cheng, Q.; Wei, L.; Liu, Z.; Ni, N.; Sang, Z.; Zhu, B.; Xu, W.; Chen, M.; Miao, Y.; Chen, L.-Q. Nature Communications 2018, 9, 2942.

He, R.; Xu, Y.; Zhang, L.; Ma, S.; Wang, X.; Ye, D.; Ji, M. Optica 2017, 4, 44-47.

Shi, L.; Zheng, C.; Shen, Y.; Chen, Z.; Silveira, E. S.; Zhang, L.; Wei, M.; Liu, C.; de Sena-Tomas, C.; Targoff, K.; Min, W. Nature Communications 2018, 9, 2995.

Yang, L.; Haagensen, J. A.; Jelsbak, L.; Johansen, H. K.; Sternberg, C.; Høiby, N.; Molin, S. Journal of Bacteriology 2008, 190, 2767-2776.

Kollef, M. H. Broad-spectrum antimicrobials and the treatment of serious bacterial infections: getting it right up front. Clinical Infectious Diseases 47, S3-S13 (2008).

Wiegand, I., Hilpert, K. & Hancock, R. E. Agar and broth dilution methods to determine the minimal inhibitory concentration (MIC) of antimicrobial substances. Nature protocols 3, 163-175 (2008).

Reller, L. B., Weinstein, M., Jorgensen, J. H. & Ferraro, M. J. Antimicrobial susceptibility testing: a review of general principles and contemporary practices. Clinical infectious diseases 49, 1749-1755 (2009).

Hrabák, J., Chudáčková, E. & Walková, R. Matrix-assisted laser desorption ionization-time of flight (MALDI-TOF) mass spectrometry for detection of antibiotic resistance mechanisms: from research to routine diagnosis. Clinical microbiology reviews 26, 103-114 (2013).

Sparbier, K., Schubert, S., Weller, U., Boogen, C. & Kostrzewa, M. Matrix-assisted laser desorption ionization-time of flight mass spectrometry-based functional assay for rapid detection of resistance against β-lactam antibiotics. Journal of clinical microbiology 50, 927-937 (2012).

Pulido, M. R., García-Quintanilla, M., Martín-Peña, R., Cisneros, J. M. & McConnell, M. J. Progress on the development of rapid methods for antimicrobial susceptibility testing. Journal of Antimicrobial Chemotherapy, dkt253 (2013).

Schröder, U.-C et al. Detection of vancomycin resistances in enterococci within 3 1/2 hours. Scientific reports 5 (2015).

Tao, Y. et al. Metabolic-Activity-Based Assessment of Antimicrobial Effects by D2O-Labeled Single-Cell Raman Microspectroscopy. Analytical Chemistry 89, 4108-4115 (2017).

Berry, D. et al. Tracking heavy water (D2O) incorporation for identifying and sorting active microbial cells. Proceedings of the National Academy of Sciences 112, E194-E203 (2015).

Liu, C.-Y. et al. Rapid bacterial antibiotic susceptibility test based on simple surface-enhanced Raman spectroscopic biomarkers. Scientific reports 6 (2016).

Cheng, J.-X. & Xie, X. S. Vibrational spectroscopic imaging of living systems: An emerging platform for biology and medicine. Science 350, aaa8870 (2015).

Evans, C. L. & Xie, X. S. Coherent anti-Stokes Raman scattering microscopy: chemical imaging for biology and medicine. Annu. Rev. Anal. Chem. 1, 883-909 (2008).

Freudiger, C. W. et al. Label-free biomedical imaging with high sensitivity by stimulated Raman scattering microscopy. Science 322, 1857-1861 (2008).

Nandakumar, P., Kovalev, A. & Volkmer, A. Vibrational imaging based on stimulated Raman scattering microscopy. New Journal of Physics 11, 033026 (2009).

Ploetz, E., Laimgruber, S., Berner, S., Zinth, W. & Gilch, P. Femtosecond stimulated Raman microscopy. Applied Physios B: Lasers & Optics 87 (2007).

Ozeki, Y. et al. Stimulated Raman scattering microscope with shot noise limited sensitivity using subharmonically synchronized laser pulses. Optics express 18, 13708-13719 (2010).

Li, J. & Cheng, J.-X. Direct visualization of de novo lipogenesis in single living cells. Scientific reports 4 (2014).

Fu, D. et al. In vivo metabolic fingerprinting of neutral lipids with hyperspectral stimulated Raman scattering microscopy. Journal of the American Chemical Society 136, 8820-8828 (2014).

(56)  References Cited

OTHER PUBLICATIONS

Wang, P. et al. Imaging Lipid Metabolism in Live Caenorhabditis elegans Using Fingerprint Vibrations. Angewandte Chemie International Edition 53, 11787-11792 (2014).

* cited by examiner a   Dried bacteria          b   Bacteria on agarose gel
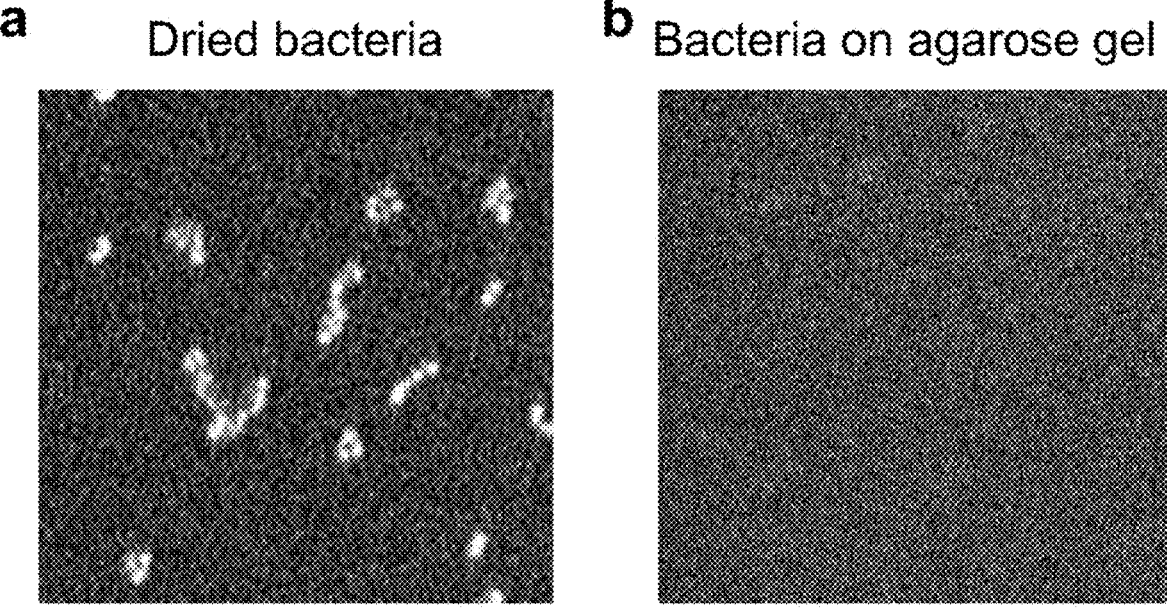
Fig. 4A                                      Fig. 4B

| Method | MIC |
|---|---|
| Culture | 1 µg/ml |
| Metabolic imaging | 2 µg/ml |

Fig. 5C

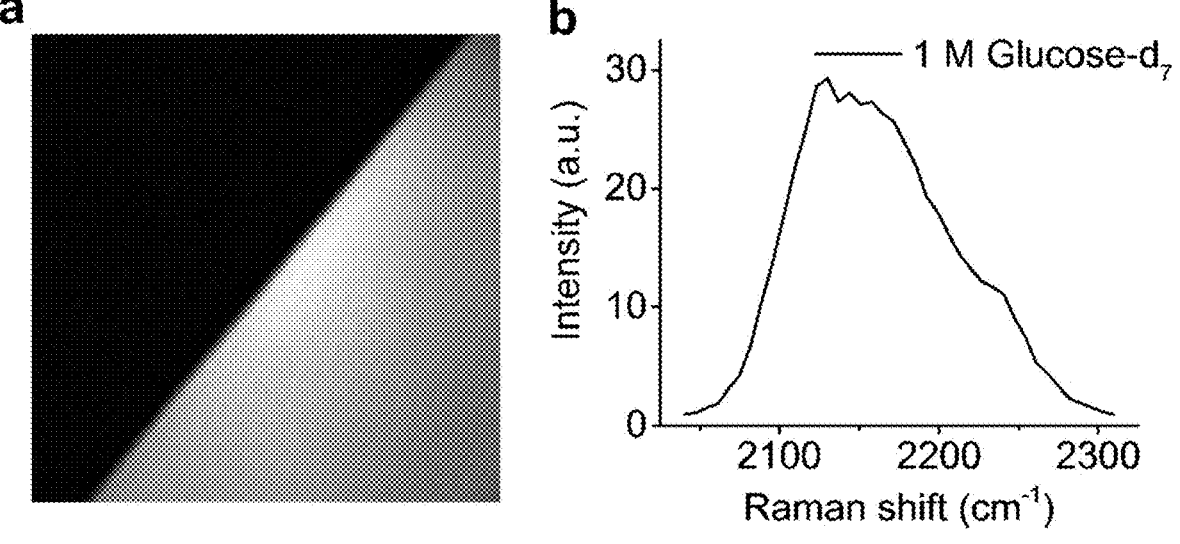
Fig. 7A                            Fig. 7B

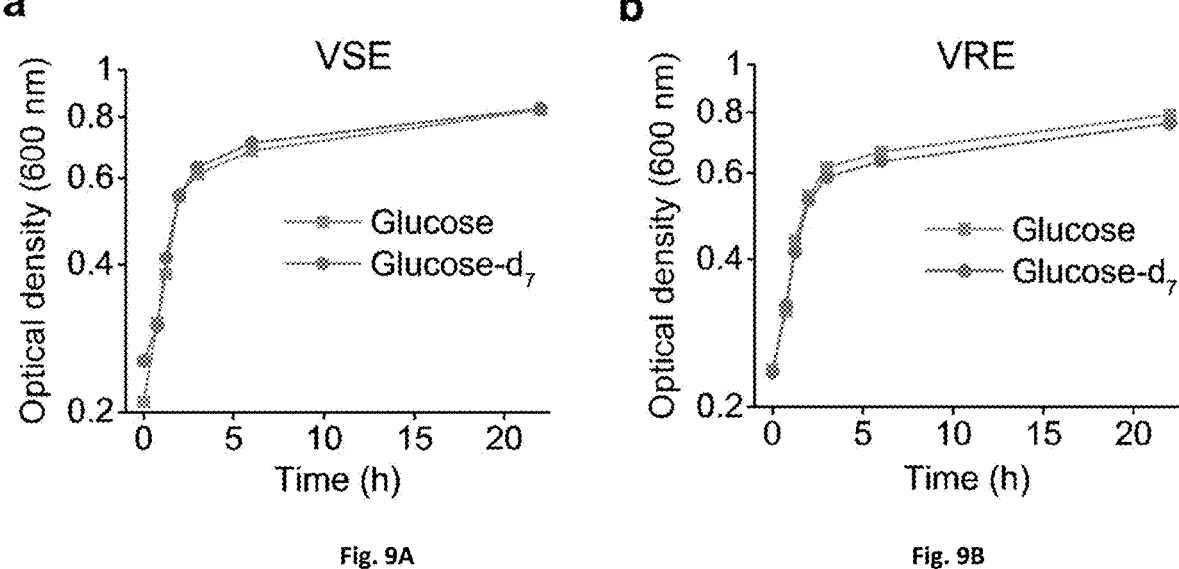
Fig. 9A                    Fig. 9B

No antibiotics       Vancomycin       Linezolid

Daptomycin       Gentamycin       Erythromycin

Fig. 17A                              Fig.17B
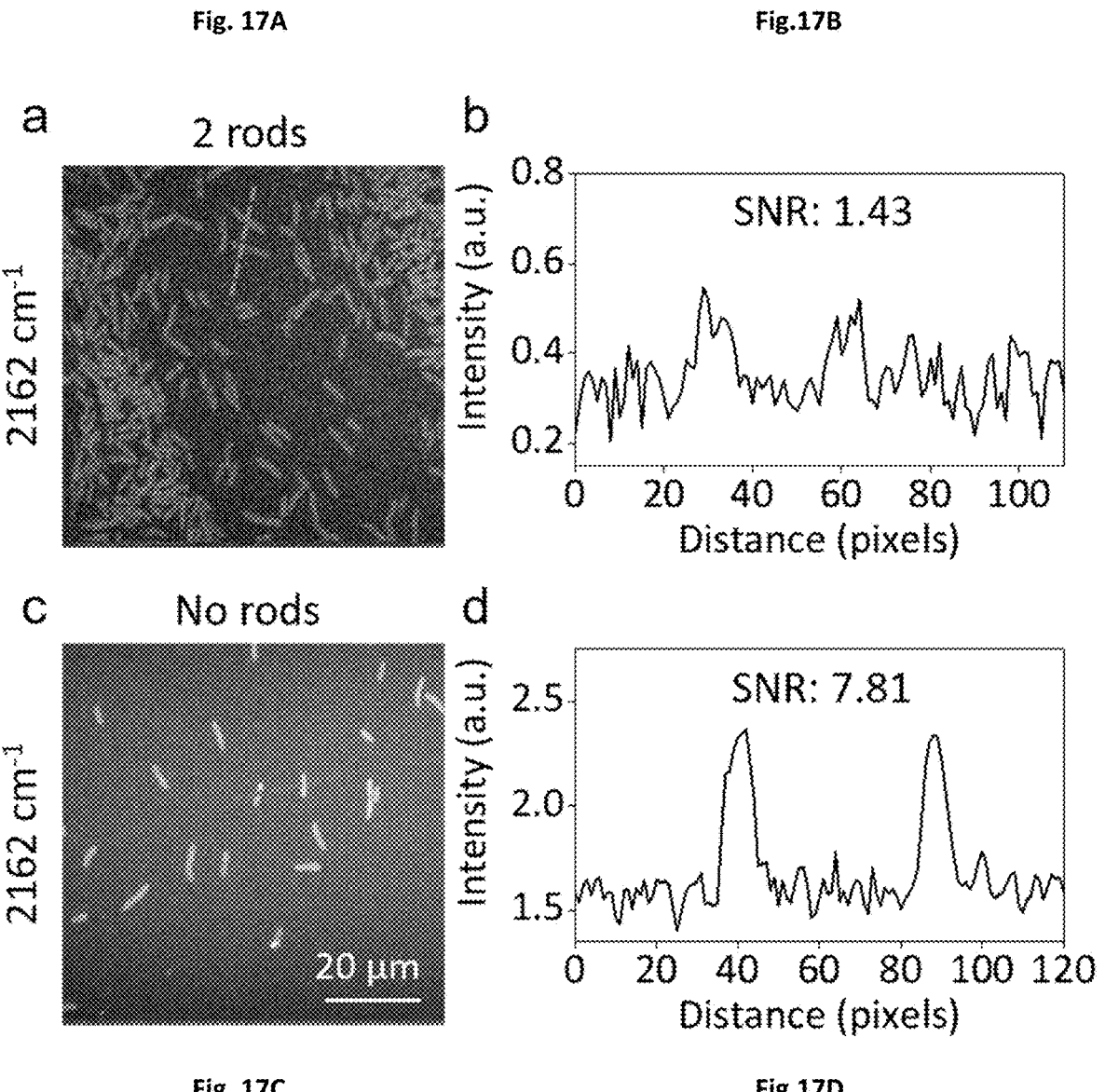
Fig. 17C                              Fig.17D

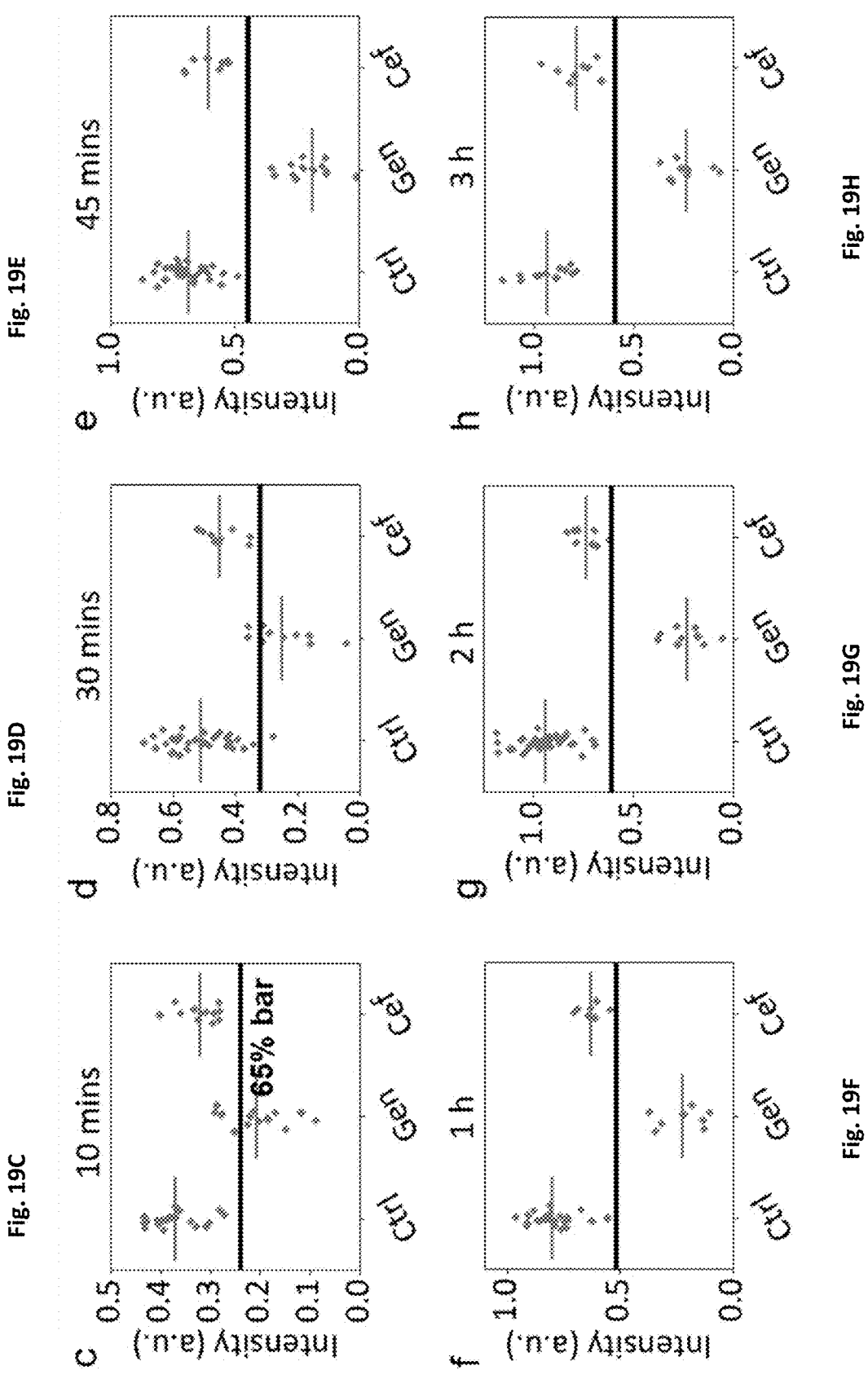

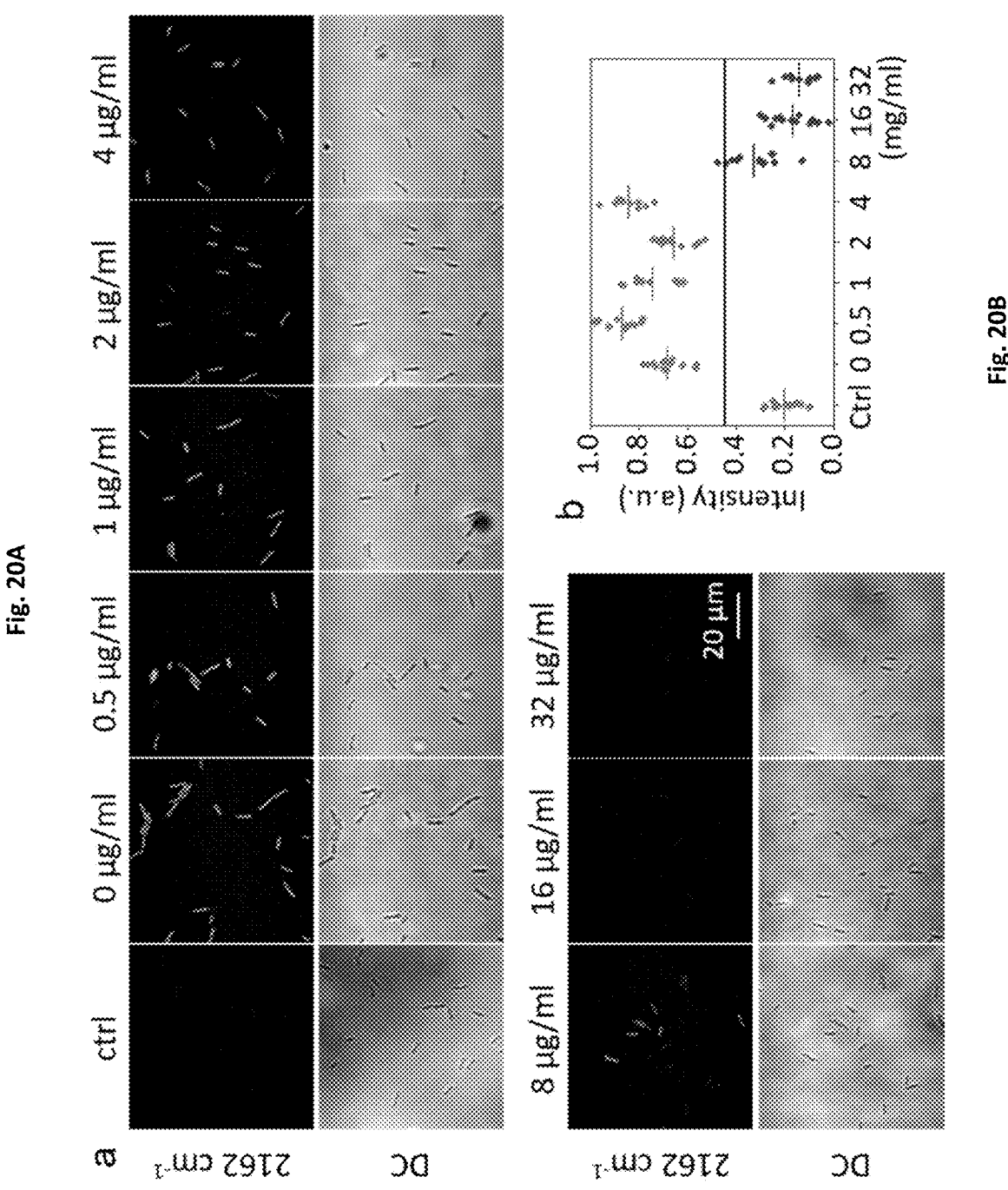

METHOD FOR THE DETERMINATION OF ANTIBIOTIC SUSCEPTIBILITY THROUGH STIMULATED RAMAN METABOLIC IMAGING

CROSS-REFERENCE TO RELATED APPLICATION

This application is a continuation application from U.S. Non-provisional patent application Ser. No. 16/645,521, which claims priority to PCT/US18/50241, which claims priority to U.S. Provisional Application 62/556,013, entitled "METHOD FOR THE DETERMINATION OF ANTIBI-OTIC SUSCEPTIBILITY THROUGH STIMULATED RAMAN METABOLIC IMAGING" filed Sep. 8, 2017, the disclosures of which is considered part of the disclosure of this application and is hereby incorporated by reference in its entirety.

FIELD OF THE INVENTION

This invention relates generally to a method for the detection of the metabolic activity of live bacteria through hyperspectral stimulated Raman scattering (SRS) micros-copy for the purpose of antibiotic susceptibility testing (AST).

BACKGROUND

Wide spread misuse and overuse of antibiotics to combat various bacterial infections has resulted in an increase in the number of resistant bacteria. Therefore, to treat certain infectious diseases it is important to profile the antibiotic response of a given bacteria though antibiotic susceptibility testing (AST). Conventional methods of AST generally utilize agar plates and broth dilution assays to grow cultures and typically require at least 16 hours to 24 hours to complete, depending upon the bacteria species. Newer tech-niques are being developed for more rapid testing, but these techniques still have limitations as they are only applicable to specific bacteria or require time consuming sample enrichment.

Raman spectroscopy, a label-free technique which mea-sures molecular vibrations, has been employed for rapid bacterial AST. Raman peaks in fingerprint region or the metabolic uptake of heavy water $D_2O$ have been used as a biomarker to characterize the response of bacteria to anti-biotic treatment. Raman spectroscopy, however, has very weak signal due to the small cross-section, and thus requires large samples or long integration time per cell. The Raman signal can be enhanced through surface-enhanced Raman spectroscopy (SERS) using metal colloids or rough metal surface, SERS has been used for rapid AST based on Raman peak change with antibiotic treatment, however, SERS needs substrate and the signals vary too much for practical use.

Coherent Raman scattering microscopy, including coher-ent anti-Stokes Raman scattering (CARS) and stimulated Raman scattering (SRS) microscopy, offers significant sig-nal improvement over spontaneous Raman. SRS micros-copy, unlike CARS, does not suffer from the non-resonant background, and has been used for metabolic imaging in cells, tissues and model organisms. However, SRS is not completely background free. Hyperspectral SRS, which records a spectrum at each pixel, has been developed to distinguish the SRS signal from background induced by nonlinear absorption and cross phase modulation.

Imaging the metabolic activity in a single bacterium remains highly challenging. The size of bacteria (~1 μm in diameter) is much smaller than that of a mammalian cell (~10 μm) and is close to the spatial resolution of CARS or SRS microscopy. Moreover, the C-D Raman signal is much weaker than the C-H signal. Therefore there exists a need for an improved method for AST. Preferably this method is performed without an extended time for sample enrichment and applicable to various bacteria's at the single cell level.

BRIEF SUMMARY OF THE INVENTION

In one aspect, this disclosure is related to a rapid antibiotic susceptibility test (AST) method applicable to all bacteria.

In another aspect, this disclosure is related to a method for monitoring the metabolic activity of glucose-$d_7$ in bacteria at the single cell level with hyperspectral stimulated Raman scattering (SRS) imaging.

In another aspect, the present disclosure is related to a rapid AST method generally applicable to all bacteria, by monitoring the metabolic activity of glucose-d7 in live bacteria at the single cell level with hyperspectral SRS imaging. The method could similarly use other nutrient sources such as D2O. Using vancomycin susceptible (VSE) and resistant (VRE) enterococci as can be used as models to show that bacteria can be detected and their metabolic activity can be quantitatively monitored at the single cell level by SRS imaging. The metabolic response to antibiotic treatment can be monitored to determine bacterial suscep-tibility and the minimum inhibitory concentration (MIC) within 30 minutes. Similarly, the imaging method can be applied for other antibiotics, regardless of their mechanism of inhibiting or killing bacteria. As a result of glucose being a common carbon source for bacterial growth, it is reason-able to anticipate that our method is generally applicable to many bacteria species.

In another aspect, this disclosure is related to a sample preparation strategy, method for an improved bacterial cul-ture medium, and imaging setup adapted to maximize the signal-to-noise ratio for more consistent image processing.

In another aspect, this disclosure is related to a Raman imaging system for rapid AST testing, wherein the Raman imaging system includes a dual output femtosecond pulse laser. The dual out femtosecond pulse layer can include a pump beam and a Stokes beam. The Stoke beam path modulated by an acousto-optical modulator. The pump beam path having a translational stage to tune a delay between the pump beam and the Stokes beam. A combiner combiner adapted to combine the pump beam and the Stokes beam. A chirping device, the chirping device adapted to form a different pulse duration between the Stoke beam and the pump beam. A laser scanning microscope can include an objective adapted to focus the pump beam and the Stokes beam on a sample. Furthermore, the system can include an oil condenser adapted to collect the laser from the sample. The system can use one or more filters positioned after the condenser and adapted to filter out the Stokes beam. A photodiode can be positioned after the filter, wherein the photodiode detects the pump beam. A lock in amplifier can be adapted to extract the pump beam signal loss.

BRIEF DESCRIPTION OF THE DRAWINGS

The features and advantages of this disclosure, and the manner of attaining them, will be more apparent and better understood by reference to the following descriptions of the disclosed system and process, taken in conjunction with the accompanying drawings, wherein:

FIG. 4A is SRS imaging at 2178 cm−1 of bacteria cultured in normal medium and dried on glass.

FIG. 4B is SRS imaging at 2178 cm−1 of bacteria cultured in normal medium and deposited on agarose gel pad.

FIG. 5C is a comparison of MIC determined from the conventional cultured based method and our metabolic imaging method.

FIG. 7A depict results from hyperspectral SRS imaging at 2150 cm$^{-1}$.

FIG. 7B is a graphical illustration of the corresponding spectrum of 1 M glucose-d$_7$ solution in C-D region.

FIG. 9A illustrates OD measurement for vancomycin susceptible enterococci cultured in M9 medium with either 2% normal glucose or 2% glucose-d7.

FIG. 9B illustrates OD measurement for vancomycin resistant enterococci cultured in M9 medium with either 2% normal glucose or 2% glucose-d7.

FIG. 11A is SRS imaging of the metabolic activity of glucose-d7 of single bacterium cultivated in normal medium for 0.5 h.

FIG. 11B is SRS imaging of the metabolic activity of glucose-d7 of single bacterium cultivated in glucose-d7 containing medium for 0.5 h.

FIG. 11C is a graph illustrating the C-D peak of a susceptible strain after being treated with oxacillin.

FIG. 11D is a graph illustrating the C-D peak of a resistant strain after being treated with oxacillin.

FIG. 17A depicts results of SRS imaging at 2162 cm−1 of *P. aeruginosa* cultivated in 70% D2O containing LB medium for 30 minutes with picosecond SRS after chirping with 2 glass SF57 rods.

FIG. 17B is an intensity plot illustrating the SNR of the imaged sample of FIG. 17A.

FIG. 17C depicts results of SRS imaging at 2162 cm−1 of *P. aeruginosa* cultivated in 70% D2O containing LB medium for 30 minutes with femtosecond SRS without chirping.

FIG. 17D is an intensity plot illustrating the SNR of the imaged sample of FIG. 17C.

FIG. 19C is an average C-D SRS intensity plots of *P aeruginosa* cultivated in 70% D2O containing LB medium without antibiotic treatment (control), and with gentamicin or cefotaxime treatment at 10 minutes.

FIG. 19D is an average C-D SRS intensity plots of *P aeruginosa* cultivated in 70% D2O containing LB medium without antibiotic treatment (control), and with gentamicin or cefotaxime treatment at 30 minutes.

FIG. 19E is an average C-D SRS intensity plots of *P aeruginosa* cultivated in 70% D2O containing LB medium without antibiotic treatment (control), and with gentamicin or cefotaxime treatment at 45 minutes.

FIG. 19F is an average C-D SRS intensity plots of *P aeruginosa* cultivated in 70% D2O containing LB medium without antibiotic treatment (control), and with gentamicin or cefotaxime treatment at 1 h.

FIG. 19G is an average C-D SRS intensity plots of *P aeruginosa* cultivated in 70% D2O containing LB medium without antibiotic treatment (control), and with gentamicin or cefotaxime treatment at 2 h.

FIG. 19H is an average C-D SRS intensity plots of *P aeruginosa* cultivated in 70% D2O containing LB medium without antibiotic treatment (control), and with gentamicin or cefotaxime treatment at 3 h.

FIG. 20A depicts results of C-D SRS imaging at 2162 $cm^{-1}$ and transmission imaging of *P. aeruginosa* cultivated in normal LB (control) or 70% D2O containing LB medium with the addition of different concentrated gentamicin.

FIG. 20B is an average SRS intensity plot of individual *P. aeruginosa* in FIG. 20A.

DETAILED DESCRIPTION OF THE INVENTION

The detailed description of various embodiments herein makes reference to the accompanying drawing figures, which show various embodiments and implementations thereof by way of illustration and best mode, and not of limitation. While these embodiments are described in sufficient detail to enable those skilled in the art to practice the embodiments, it should be understood that other embodiments may be realized and that mechanical and other changes may be made without departing from the spirit and scope of the present disclosure. Furthermore, any reference to singular includes plural embodiments, and any reference to more than one component may include a singular embodiment. Likewise, any ordination of a device or of a component or portion of a device with designations such as "first" and "second" is for purposes of convenience and clarity and should not be construed as limiting or signifying more than an arbitrary distinction. Moreover, recitation of multiple embodiments having stated features is not intended to exclude other embodiments having additional features or other embodiments incorporating different combinations of the stated features.

Systems, methods and computer program products are provided in various embodiments of the present disclosure. References to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Figure 1A:
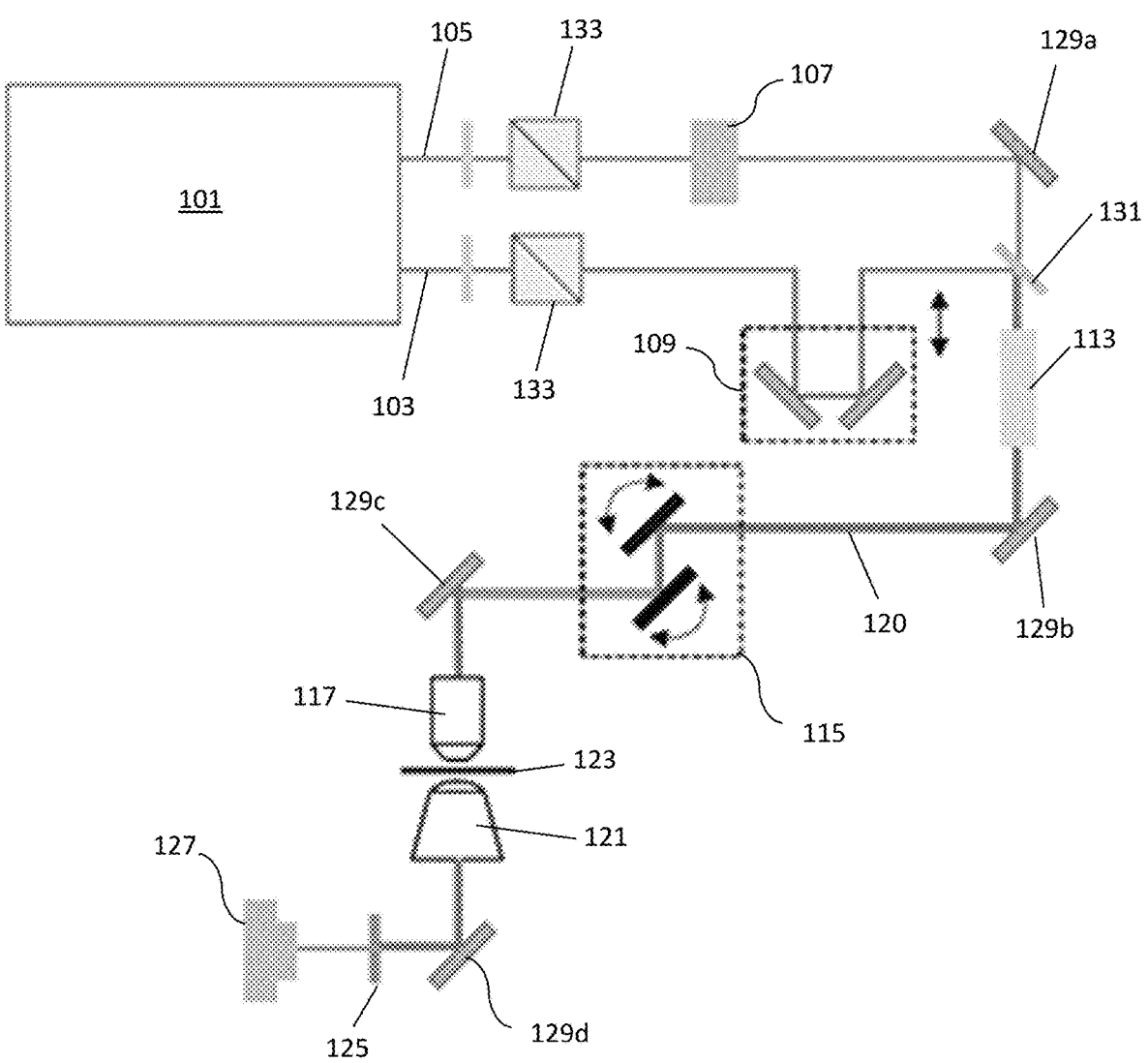
FIG. 1A is an illustration of an exemplary hyperspectral SRS imaging setup, according to the present disclosure.
Figure 1B:
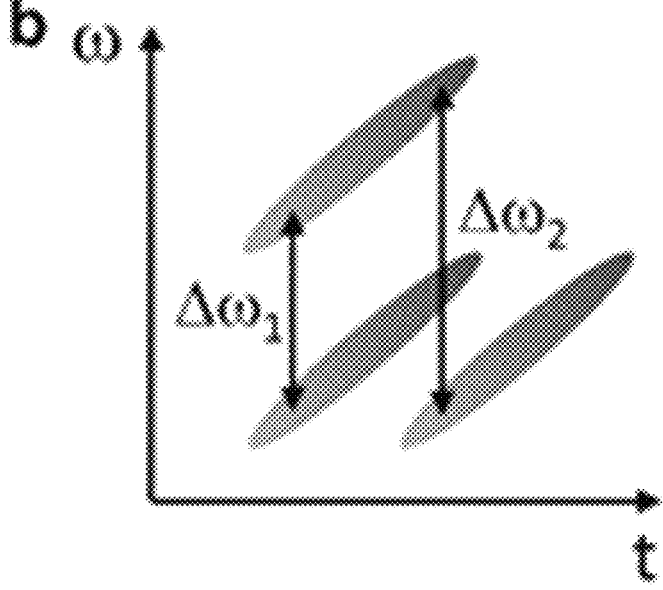
FIG. 1B is an illustration of the delay between the pump and Stokes after chirping, according to the present disclosure.

Referring now to FIGS. 1A-1B, of the method for the determination of antibiotic susceptibility through Raman metabolic imaging. The imaging system can include any type of Raman imaging, including but not limited to, stimulated Raman scattering imaging, coherent anti-Stokes Raman scattering imaging, or coherent Raman induced Kerr effect imaging. In one exemplary embodiment, the present disclosure a hyperspectral stimulated Raman scattering (SRS) imaging setup is disclosed. Within the imaging system of present disclosure, the system can include a light source 101. In one exemplary embodiment, the light source can be a dual output femtosecond pulse laser (InSight DeepSee, Spectra-Physics) that can have a repetition rate at about 80 MHz, however, any suitable rate can be used. The light source 101 can be employed for hyperspectral SRS imaging. Similarly, the imaging system can use single color SRS imaging. The imaging at C-D vibration region can be carried out using a light source 101, such as a tunable laser 103. In one exemplary embodiment the tunable laser can be a 120-fs tunable laser that is tuned to about 847 nm. Additionally, filters can be incorporated to clear the laser beam. This beam 103 can serve as the pump beam. A second light beam 105, such as a 220 fs laser centered at about 1040 nm. The second beam 105 can serve as a Stokes beam, that can be modulated by an acousto-optical modulator 107 (AOM, 1205-C, Isomet) at 2.35 MHz. Each of the beams can pass through one or more filters or lenses. Similarly, each beam can pass through a polarized beam splitter (PBS) 133. In one exemplary embodiment, A motorized translational stage 109 (T-LS28E, Zaber) can be installed in the pump path to tune the delay between the pump beam 103 and Stokes beams 105. The two beams can then be combined using a combiner 111. Both beams can then be chirped with one or more glass rods 113. In one exemplary embodiment, two glass rods having a length of about 15 cm long can be used. Similarly, the glass rods can be SF57 glass rods.

After chirping, the pulse durations of pump and Stokes in some exemplary embodiments can be between about 1-2 ps, or between 1.3 and 1.9 ps. In one exemplary embodiment the pump and Stoke beams can be about 1.9 ps and 1.3 ps, respectively. In other embodiments, the imaging system may not use the chirping of the beams. The pump 103 and Stokes 105 beams may then be directed into laser scanning microscope having a scanning unit 115 and one or more lenses 117. In one exemplary embodiment, the lens 117 can be about a 60× water objective lens (NA=1.2, UPlanApo/IR, Olympus) that can be used to focus the lasers to sample 119. An oil condenser 121 (NA=1.4, U-AAC, Olympus) can be used to collect the combined laser beam 120 from sample 123. One or more filters 125 (HQ825/150m, Chroma) can be used to filter out the Stokes beam, the pump beam was detected by a photodiode 127 ((S3994-01, Hamamatsu) and the pump beam loss signal can be extracted by a lock-in amplifier (HF2LI, Zurich Instrument). The system can include one or more mirrors to direct each beam throughout various components of the apparatus. In some exemplary embodiments, one or more mirrors 129 can be dichromic mirrors 131. As shown in FIG. 1B, the Awl and Awl illustrate possible Raman peak that can be measured by an exemplary imaging system of the present disclosure. Each delay between the pump and Stokes after chirping can correspond to a molecular vibration mode detected by the imaging system.

The present disclosure also relates to an exemplary method preparing samples for use with an exemplary imaging system, including but not limited to SRS imaging systems. The sample preparation method can utilize a bacteria immobilization pad. In one exemplary embodiment, the immobilization pad can include an agarose gel pad for the placement of bacteria in solution to the gel pad for live imaging. In some exemplary embodiments, the agarose gel pad can be prepared according to the following steps: (1) 1% in weight agarose powder is added to about 2 mL purified water in a plastic tube, (2) the tube can be heated in a microwave for about 20 second until the agarose powder is completely melted, (3) about 10 µL of the heated agarose gel solution can be added to a cover glass by a pipette, (4) a second cover glass can be immediately placed on top of the agarose gel solution to make it flat and generally sandwiching the gel solution between the first cover glass and the second cover glass, (5) after about 2 minutes one of the cover glasses is removed from the agarose gel by sliding the two cover glasses, (6) the agarose gel remaining on one of the cover glasses is solid and became a pad.

The AST procedure of the present disclosure uses an AST of bacteria can be determined within one cell cycle (about 30 minutes) by measuring the metabolic activity in bacteria with Raman imaging, such as stimulated Raman scattering (SRS) microscopy. The imaging can monitor the metabolic activity of deuterated glucose, such as glucose-d$_7$, with chirped picosecond SRS at C-D vibrational frequency, and use the C-D signal as a marker to perform AST.

Similarly, water can also be used for biomolecule synthesis in bacteria, and its metabolism can be monitored using heavy water (D$_2$O) at C-D frequency with Raman spectroscopy. Unlike glucose-d$_7$, D$_2$O itself does not have C-D bond, and as a result D$_2$O metabolic activity may provide a better contrast for rapid AST that the glucose-d$_7$. The metabolic activity of D$_2$O has been used to image the metabolic active bacteria with spontaneous Raman spectroscopy. SRS imaging has orders-of-magnitude signal enhancement, thereby enabling high speed imaging. Additionally, SRS imaging of D$_2$O metabolism is a noninvasive and accurate method to visualize metabolic dynamics in mammalian cells and animals.

The SRS imaging based method of the present disclosure can determine the susceptibility of bacteria to antibiotics within about 10 minutes. A bacteria solution for testing through SRS imaging and placement on the agarose gel pad can be prepared by cultivating bacteria in a broth, such as a Lysogeny broth (LB) (LB Broth, Sigma Aldrich) for about two hours to reach to log phase. The bacteria can then added in a ratio between about 0.1:100 to about a 10:100 ratio to 2 mL of various types of medium. In one exemplary embodiment, the ration can be about 1:100 to 2 ML of medium, such as a specialized medium. Some exemplary embodiments can use D$_2$O medium or other specialized medium herein referred to as M9 medium wherein about a 2% glucose-d$_7$ can be only carbon source. The M9 medium is developed and selected to maximize the signal within the C-D vibrational region. To measure the resistance of a given bacteria to an antibiotic, the antibiotic is added to the specialized medium to a concentration of about 20 µg/mL. After at least about 30 minutes of incubation about 500 µl of the sample is centrifuged, washed twice with purified water, and deposited to an agarose gel pad for imaging. An imaging setup of illustrated in FIG. 1A can be utilized to process the sample.

Figure 2A:
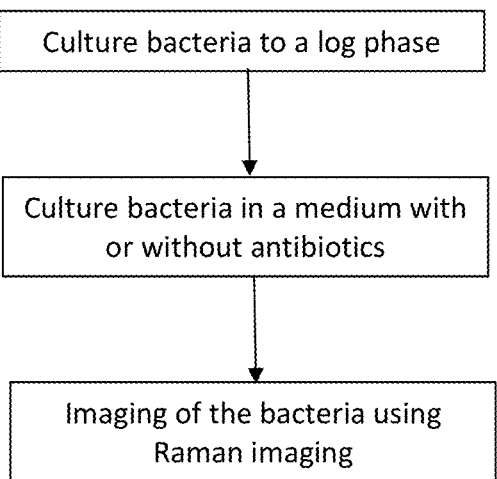
FIG. 2A illustrates a process for the AST procedure, according to the present disclosure.

Referring now to FIG. 2A-D the method of the present disclosure can generally be performed in an exemplary method to determine effectiveness utilizing an antibiotic, such as vancomycin. Accordingly, the method can be utilized to examine the influence of antibiotics to the metabolic uptake of glucose-d$_7$ by bacteria. Vancomycin susceptible (VSE) and Vancomycin resistant (VRE) enterococci *E. faecalis* can first be grown to a log phase by cultivating in LB medium for about 2 hours, then VSE and VRE can further be cultivated in M9 medium with about 2% glucose-d$_7$ as the sole carbon source, respectively, with the addition of vancomycin to a final concentration of about 20 µg/mL (FIG. 2A). Other embodiments can include various types of carbon source as a sole carbon source or in combination with other carbon or nutrient sources. One exemplary embodiment can use a nutrient source of about 0-100% deuterium dioxide. Similarly, the carbon source can include a combination of deuterium dioxide and glucose-d$_7$. This concentration was chosen because it is between the minimum inhibitory concentrations (MICS) of vancomycin to VSE (MIC is 1 µg/mL) and to VRE (MIC is >100 µg/mL). For control, VSE and VRE were cultivated in glucose-d$_7$ containing medium without the addition of vancomycin (FIG. 2*a*). After 30 minutes (0.5 hours) to 3 hours incubation, each sample was centrifuged and washed twice in water, and then deposited on an agarose gel pad for SRS imaging.

Figure 2B:
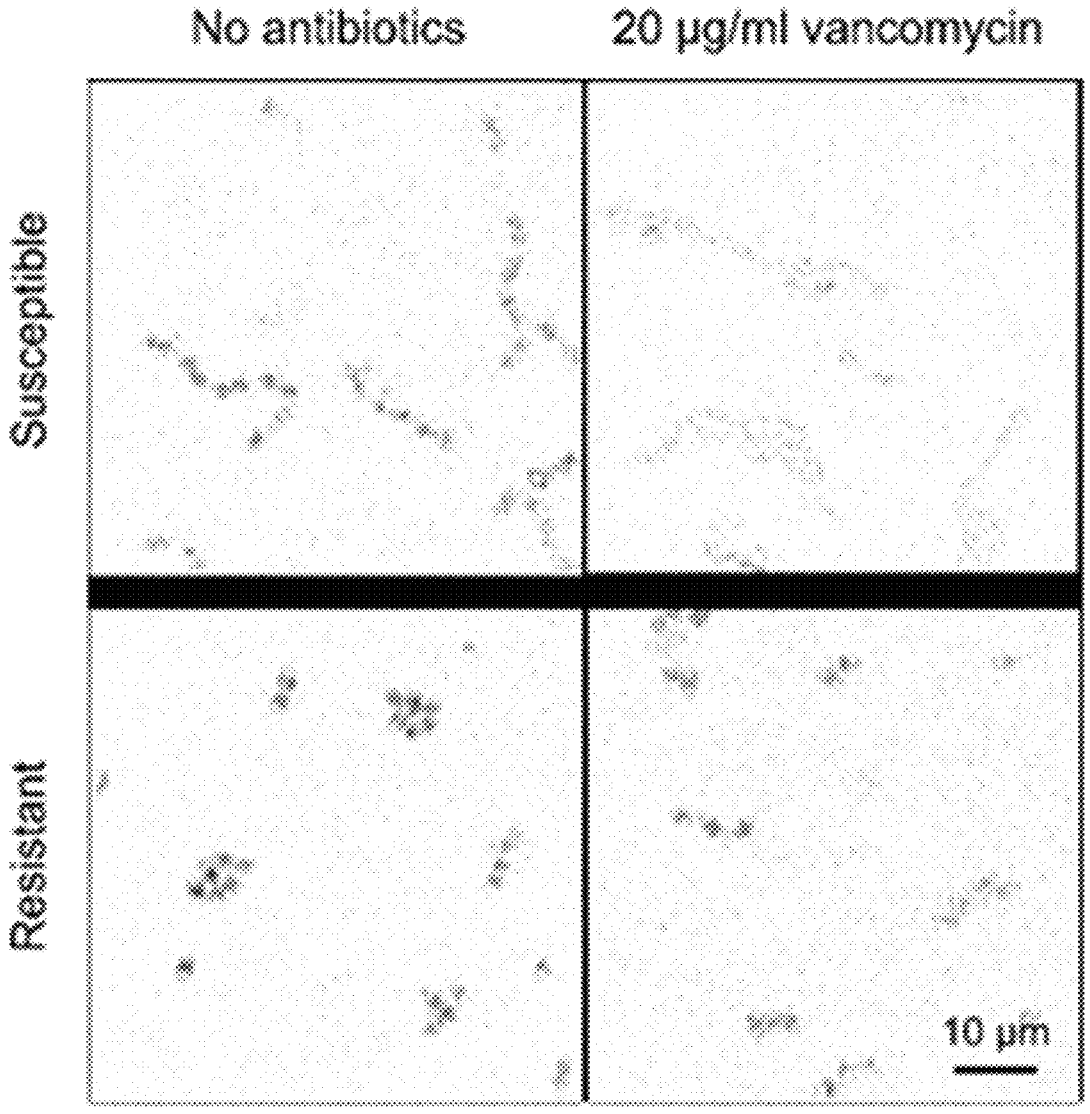
FIG. 2B illustrate SRS image data at C-D vibrational region (2178 cm$^{-1}$) for vancomycin susceptible and resistant *E. faecalis* with and without 20 µg/ml vancomycin treatment, according to the present disclosure.

FIG. 2B shows the SRS imaging at C-D vibration region (~2160 cm$^{-1}$) for VSE and VRE cultivated in glucose-d$_7$ containing medium for 30 minutes, with and without the addition of vancomycin. In the control group, both VSE and VRE have a strong C-D signal, indicating high metabolic uptake of glucose-d$_7$ by bacteria, and individual bacterium can be clearly observed. In the vancomycin treated group, the intensity of C-D signal for individual VSE have been reduced to about ⅓ of the intensity of C-D signal for individual VSE in the control group. Since the SRS signal intensity of glucose-d$_7$ is proportional to its concentration, the reduced signal indicates less glucose-d₇ uptake. On the contrary, the intensity of C-D signal for individual VRE is similar to the control group.

Figure 2C:
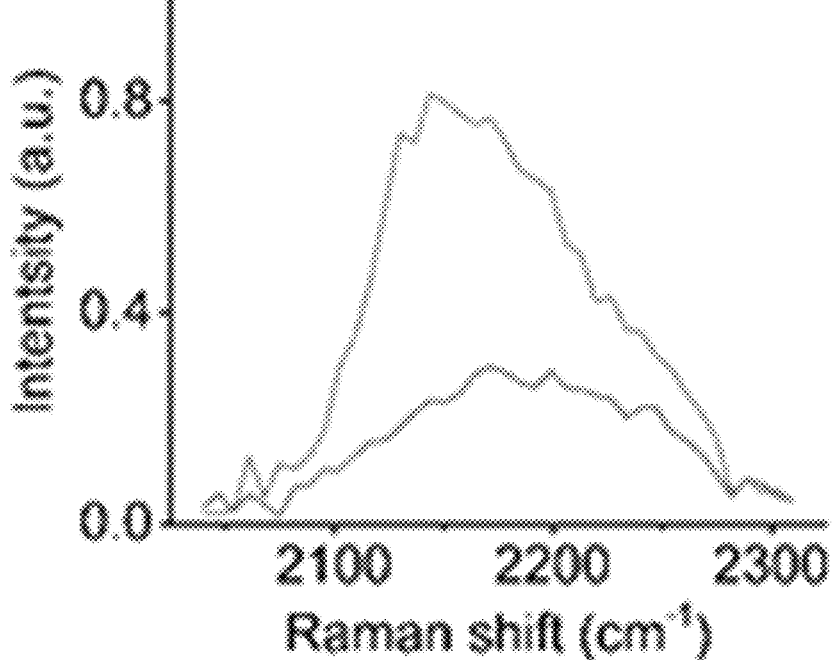
FIG. 2C illustrate SRS spectra data for susceptible bacteria, according to the present disclosure.
Figure 2D:
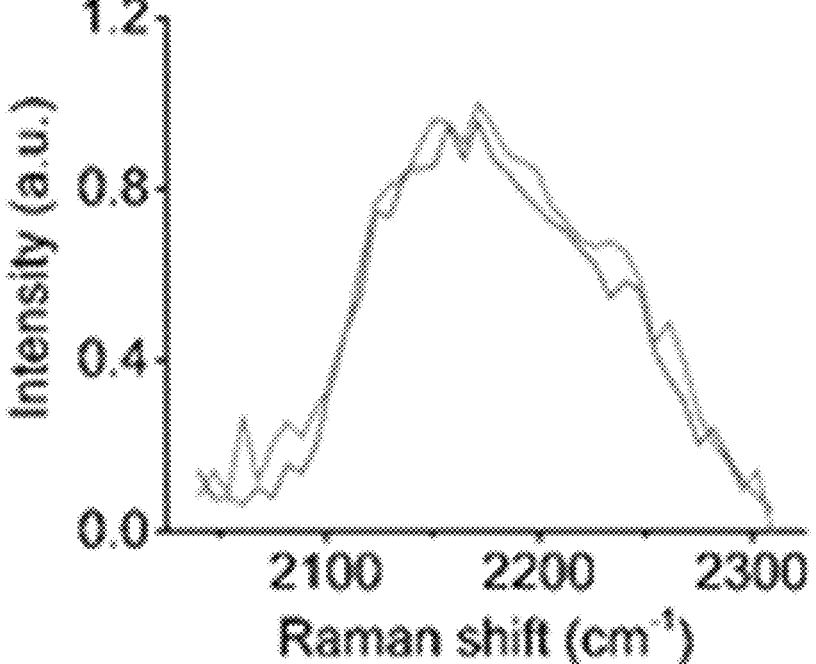
FIG. 2D illustrate SRS spectra data for resistant bacteria, according to the present disclosure.
Figures 3A, 3B, 3C, 3D:
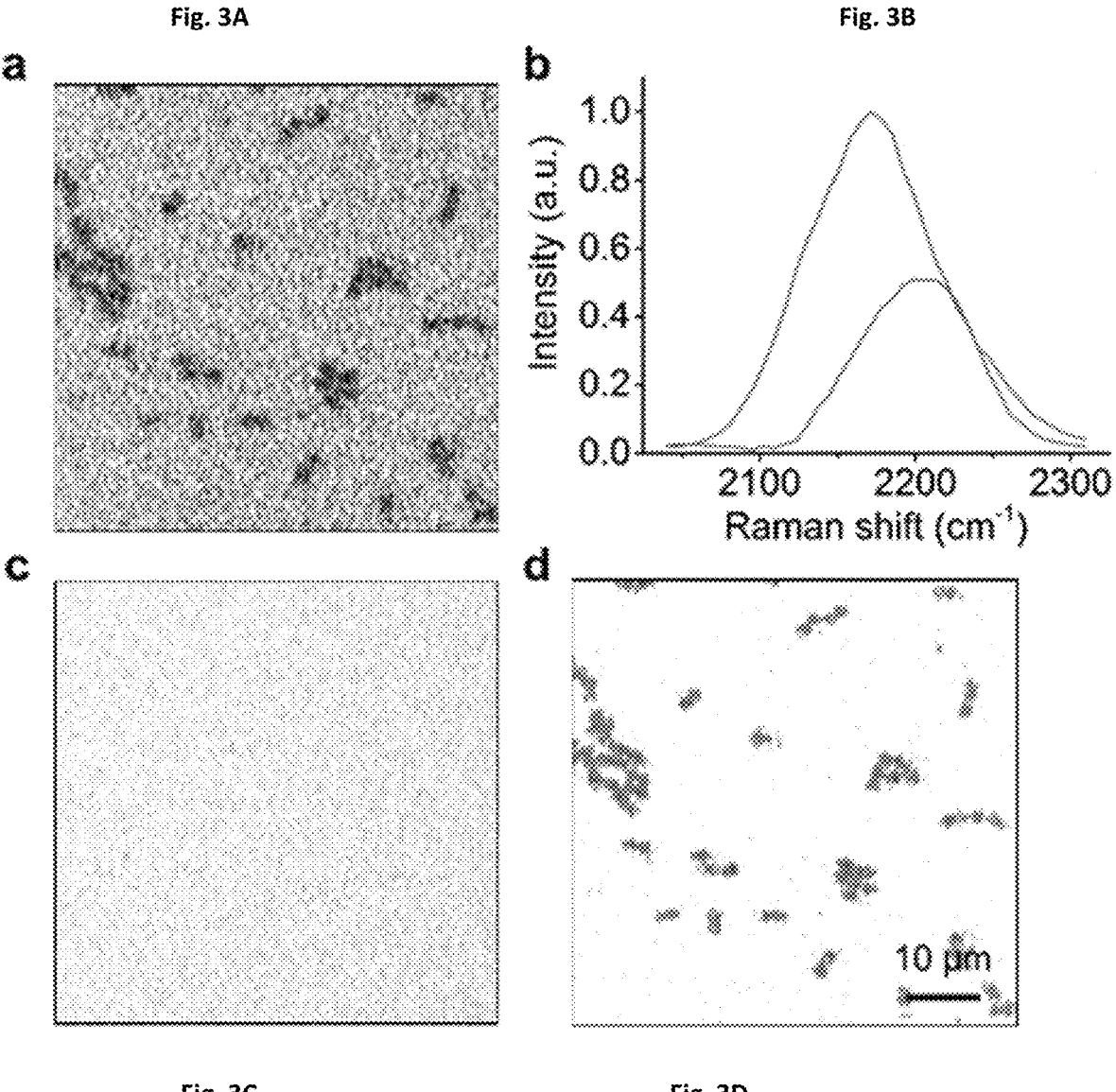
FIG. 3A is the SRS image at the C-D vibrational region for bacteria deposited on agarose gel.
FIG. 3B is the multivariate curve resolution (MCR) analysis data for hyperspectral SRS imaging data to separate the C-D component of bacteria from the gel background, according to the present disclosure, including the SRS image at the C-D vibrational region for bacteria deposited on agarose gel, the MCR output spectra of glucose-d$_7$ and gel components.
FIG. 3C is the SRS image at the D vibrational region of the gel component after MCR.
FIG. 3D is the SRS image of the glucose-d$_7$ component after MCR.

FIGS. 2C and 2D show the corresponding normalized SRS spectra of VSE and VRE shown in FIG. 2A. All spectra show a peak in the C-D vibration region, however, vancomycin treatment reduced the signal intensity of VSE compared to the control, while the signal intensity of VRE remain the same with and without vancomycin treatment, which is consistent with the SRS imaging shown in FIG. 2B. These results indicate that the metabolic activity of VSE and VRE respond differently to vancomycin treatment, therefore the susceptibility of VSE and VRE can be determined within 30 minutes, this is close to one cell cycle of *E. faecalis*. Similar effects were observed for 1 hour and 3 hours vancomycin treatment, therefore the AST of *E. faecalis* by the presently disclosed imaging method is not time sensitive.

To quantify the C-D content of the *E. faecalis* cells and the response of bacteria to the treatment of antibiotics, multivariate curve resolution (MCR) analysis is applied to retrieve the C-D component from hyperspectral SRS imaging data shown in FIGS. 3A-D. MCR is a bilinear model which decomposes the experimental data matrix that contains spectrum at each pixel into concentration maps and spectra of principle components. With an initial estimated spectrum of each component as the input, MCR is calculated and optimized iteratively using alternating least squares algorithm until convergence is reached. The output of MCR contains the concentration map and spectrum of each component. Referring now to FIG. 3A-D the spectra of glucose-d₇, which represented the C-D component, and gel, which represented the background, were used as the input components. After MCR analysis, C-D component can be clearly separated from the background and utilized to quantify the contents of the collected SRS imaging data.

Although the present method generally discloses hyperspectral SRS microscopy for the metabolic imaging based AST, another exemplary embodiment may use single frequency SRS microscopy with the improved sample preparation of the method. Previous results for single frequency SRS utilized bacteria that were dried on glass to avoid the movement of bacteria during measurement, this caused strong noise in the SRS signal. The agarose gel sample preparation and depositing bacteria in solution on the agarose gel pad to keep bacteria alive, removes the noise. In this way the SRS signal of bacteria in C-D vibrational frequency is mostly from the C-D component. Therefore, the metabolic imaging based AST method by monitoring the C-D component change of bacteria can be detected by single frequency SRS imaging, which takes much less time than hyperspectral SRS imaging since only one image, instead of an image stack, is taken.

Furthermore, anther exemplary embodiments can use additional steps to prepare samples. In one exemplary embodiments prepared samples for SRS imaging by drying bacteria on a glass. As depicted in FIG. 4A-B, Bacteria deposited on agarose gel significantly reduced the cross-phase modulation noise of SRS imaging. FIG. 4A is SRS imaging at 2178 cm−1 of bacteria cultured in normal medium and dried on glass, whereas FIG. 4B depicts SRS imaging at 2178 cm−1 of bacteria cultured in normal medium and deposited on agarose gel pad. A strong background was found on the imaging using the dried bacteria on glass that was possibly due to cross-phase modulation. An agarose gel pad was used and bacteria was deposited in solution to this gel pad for live bacteria imaging. This sample preparation significantly reduced the background in SRS imaging, as shown in FIG. 4B. To maximize the C-D signal level, the culture medium was replaced from LB medium which contains normal glucose to custom-made M9 medium, in which glucose-d₇ is the only carbon source, and increased the glucose-d₇ concentration to 2%. To ensure signal and spectral resolution, a two rods setup was adopted using two 15 cm long SF57 glass rods to chirp the pump and Stokes beams for the hyperspectral SRS imaging, and achieve a SNR of about 5 for a single bacterium at the C-D vibrational region, with a spectral resolution about 20 cm⁻¹.

To test the toxicity of glucose-d7 to bacteria, *E. faecalis* 31970 and 31972 were cultivated in custom-made M9 medium, one with normal glucose for control and the other with glucose-d7. The growth of bacteria was monitored by optical density (OD) measurement at 600 nm for up to 22 hours (FIG. 9). Similar growth curves were observed for both *E. faecalis* 31970 and *E. faecalis* 31972 cultivated in control and glucose-d7 containing medium, indicating no toxicity of glucose-d7 to bacterial growth. FIG. 9A illustrates OD measurement for vancomycin susceptible enterococci cultured in M9 medium with either 2% normal glucose or 2% glucose-d₇, whereas FIG. 9B illustrates OD measurement for vancomycin resistant enterococci cultured in M9 medium with either 2% normal glucose or 2% glucose-d₇.

Figure 5A:
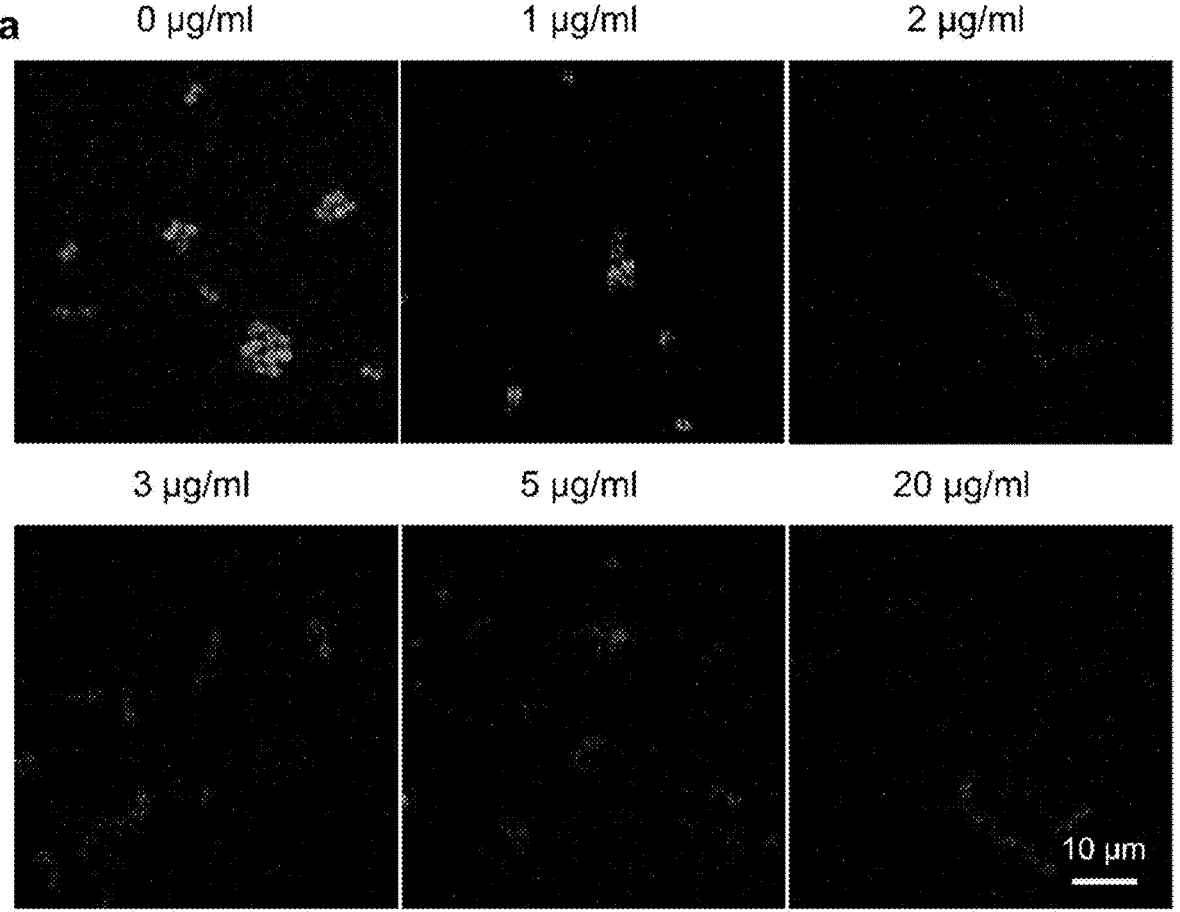
FIG. 5A the C-D component of each sample after MCR analysis.
Figure 5B:
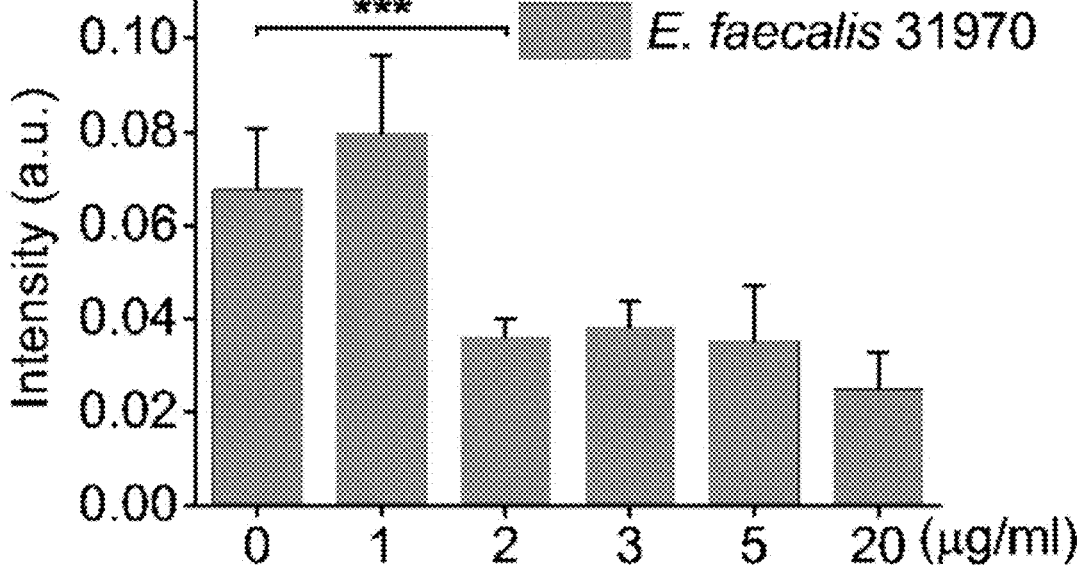
FIG. 5B illustrates the intensity of C-D component for individual bacterium in field of view for the change of glucose-d7 uptake in bacteria with vancomycin treatment.

The MIC, defined as the lowest concentration of antibiotic that is able to inhibit the visible growth of bacteria in vitro, can be determined by our metabolic imaging method. VSE was cultured in glucose-d7 containing M9 medium, with the addition of different concentrations of vancomycin. After 1 hour of cultivation, each sample was centrifuged, washed twice in PBS and deposited on an agarose gel pad for SRS imaging. FIG. 5A shows the C-D component of each sample after MCR analysis. To quantitatively compare the change of glucose-d7 uptake in bacteria with vancomycin treatment, the intensity of C-D component for individual bacterium in field of view was statistically analyzed and plotted (FIG. 5B). Compared to the control without vancomycin treatment, 2 µg/mL or higher concentrations of vancomycin treatment significantly reduced the intensity of C-D component. On the contrary, 1 µg/mL vancomycin treatment did not reduce this intensity. Therefore, the MIC for VSE determined by our metabolic imaging method is 2 µg/mL, which is 2 times of the MIC determined by conventional cultured based method. This discrepancy is acceptable and within the precision range, largely due to the practice of manually serial dilution of the antibiotics in conventional AST. FIG. 5A depicts results of a C-D component concentration map for bacteria cultured in glucose-d₇ containing medium for 1 hour, at different vancomycin concentrations. FIG. 5B is a graph illustrating a quantitation of C-D component intensity. The C-D component intensity for bacteria with 2 µg/ml and higher vancomycin treatment shows significant decrease compared to the control without vancomycin treatment. As shown in FIG. 5C, a comparison of MIC determined from the conventional cultured based method and our metabolic imaging method.

Figure 8:
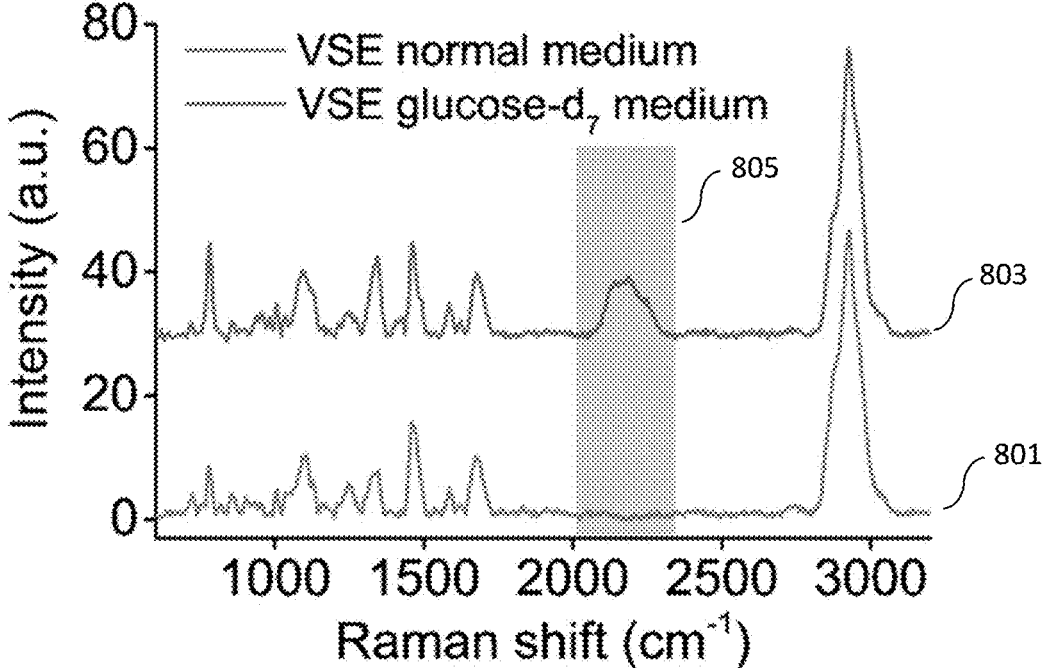
FIG. 8 depict results of spontaneous Raman spectra of VSE cultivated bacteria in normal medium and 2% glucose-d$_7$ containing medium.
Figures 10A, 10B, 10C, 10D, 10E, 10F:
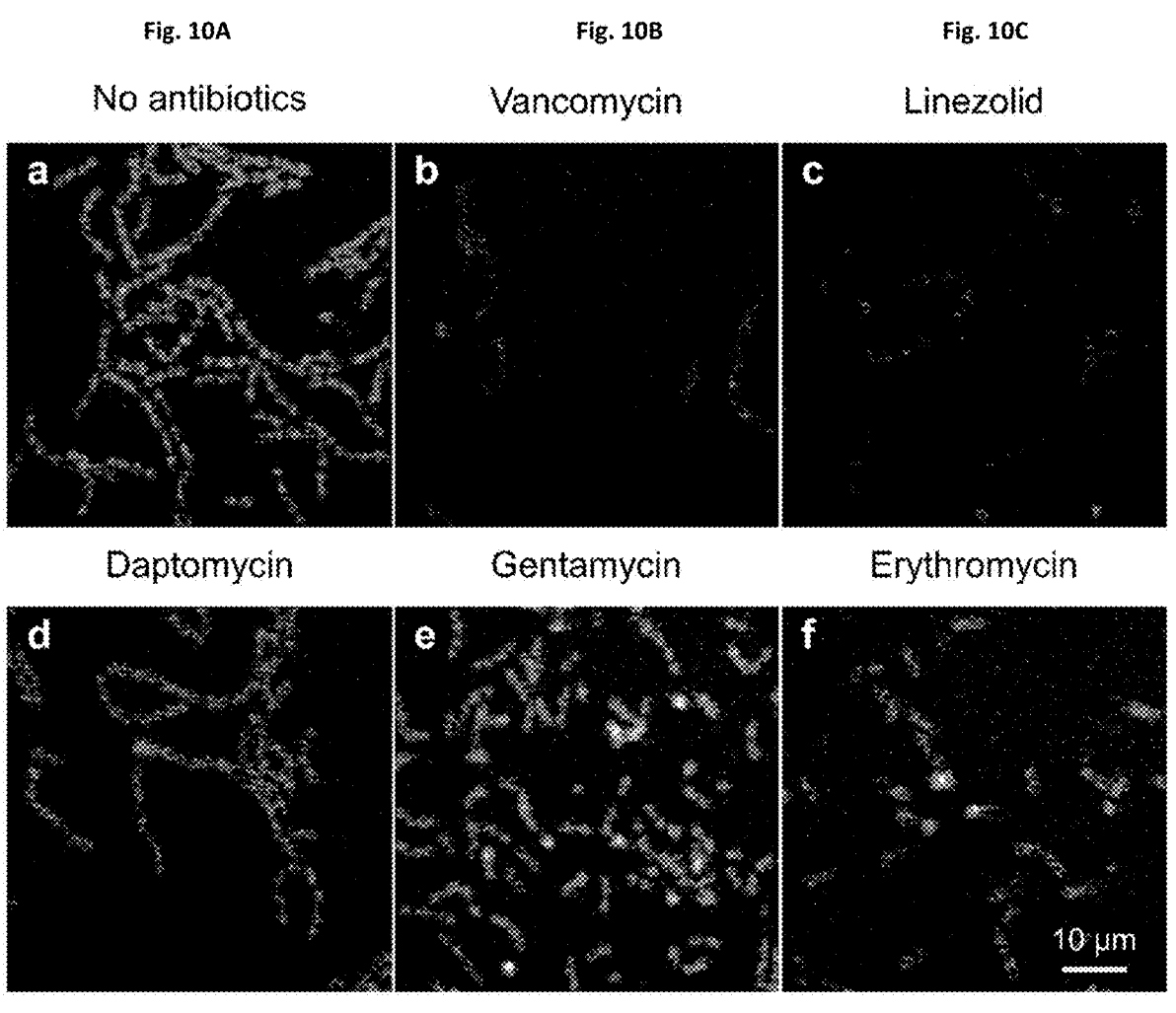
FIG. 10A depict SRS metabolic imaging results of antibiotic susceptibility testing of *E. faecalis* 31970 with no antibiotics.
FIG. 10B depict SRS metabolic imaging results of antibiotic susceptibility testing of *E. faecalis* 31970 to vancomycin.
FIG. 10C depict SRS metabolic imaging results of antibiotic susceptibility testing of *E. faecalis* 31970 to linezolid.
FIG. 10D depict SRS metabolic imaging results of antibiotic susceptibility testing of *E. faecalis* 31970 to daptomycin.
FIG. 10E depict SRS metabolic imaging results of antibiotic susceptibility testing of *E. faecalis* 31970 to gentamycin.
FIG. 10F depict SRS metabolic imaging results of antibiotic susceptibility testing of *E. faecalis* 31970 to erythromycin.

Assessing bacterial metabolic activity by SRS imaging was tested by cultivated *E. faecalis* in normal glucose 801 and glucose-d7 803 containing medium, then washed in PBS to remove traces of the culture medium, and deposited on agarose gel pads for SRS imaging. Hyperspectral SRS imaging of 1 M glucose-d7 solution as depicted in FIG. 7B, shows a peak around 2130 cm−1, from the C-D vibration modes. This peak lies in the cell silent region of Raman spectrum, providing an excellent contrast for imaging the metabolic uptake of deuterium labeled metabolite. SRS imaging of bacteria cultivated in glucose-d7 containing medium show a strong signal at the C-D vibrational region, indicating success uptake and utilization of glucose-d7. For control, no signal was observed for bacteria cultivated in normal glucose medium. These results were further confirmed by spontaneous Raman measurement as shown in FIG. 8, where a peak in C-D region was observed for bacteria cultivated in glucose-d 7 803 containing medium only. These data collectively showed that the metabolic activity of glucose-d7 uptake by bacteria can be monitored by hyperspectral SRS imagine at the single cell level. The grey bar 805 indicates the C-D region around 2150 cm$^{-1}$.

Figures 6A, 6B, 6C, 6D:
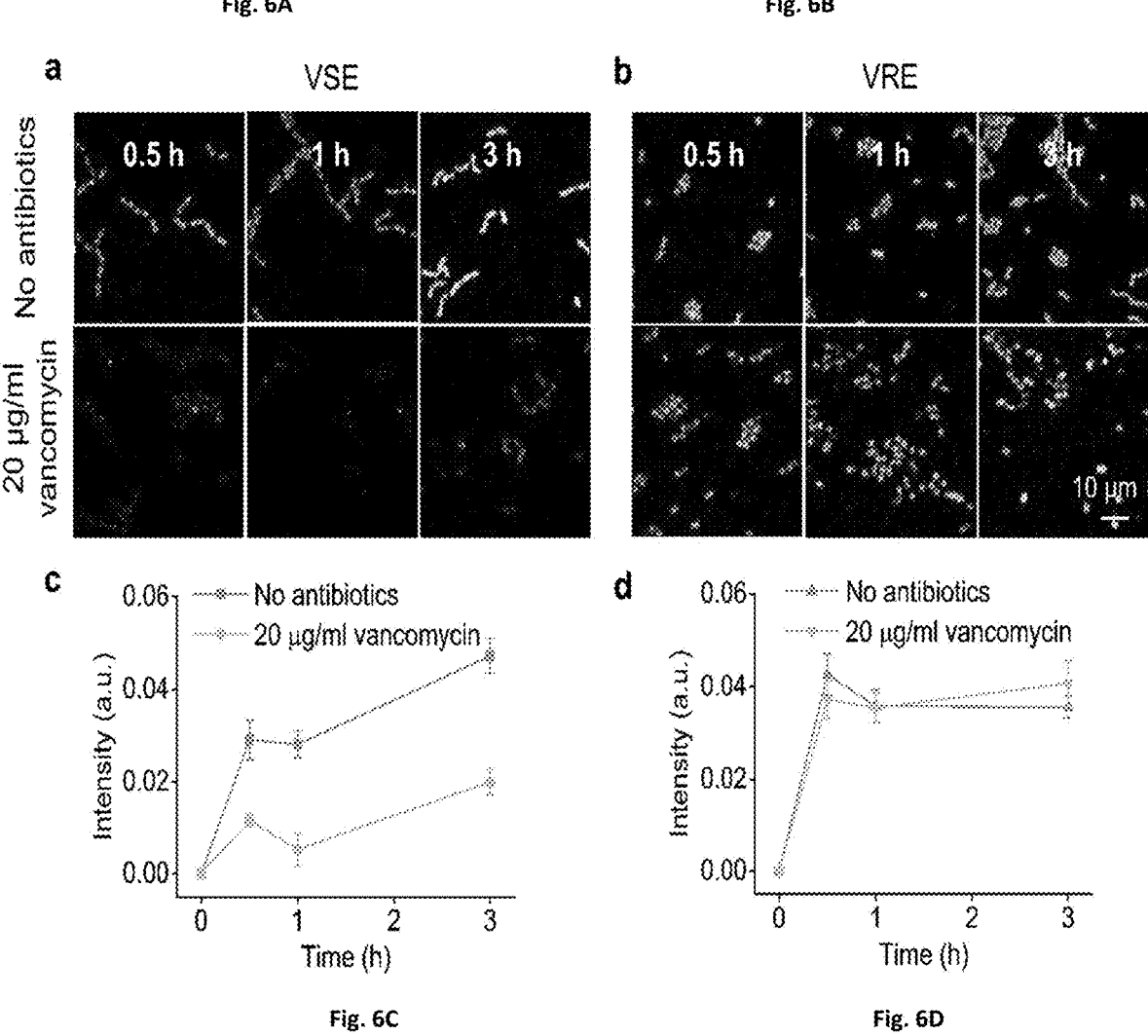
FIG. 6A are images showing the temporal dynamics of C-D component after MCR analysis for VSE.
FIG. 6B are images showing the temporal dynamics of C-D component after MCR analysis for VRE.
FIG. 6C is a graph showing the average intensity of C-D component in individual bacteria for VSE.
FIG. 6D d is a graph showing the average intensity of C-D component in individual bacteria for VRE.
Figures 13A, 13B, 13C:
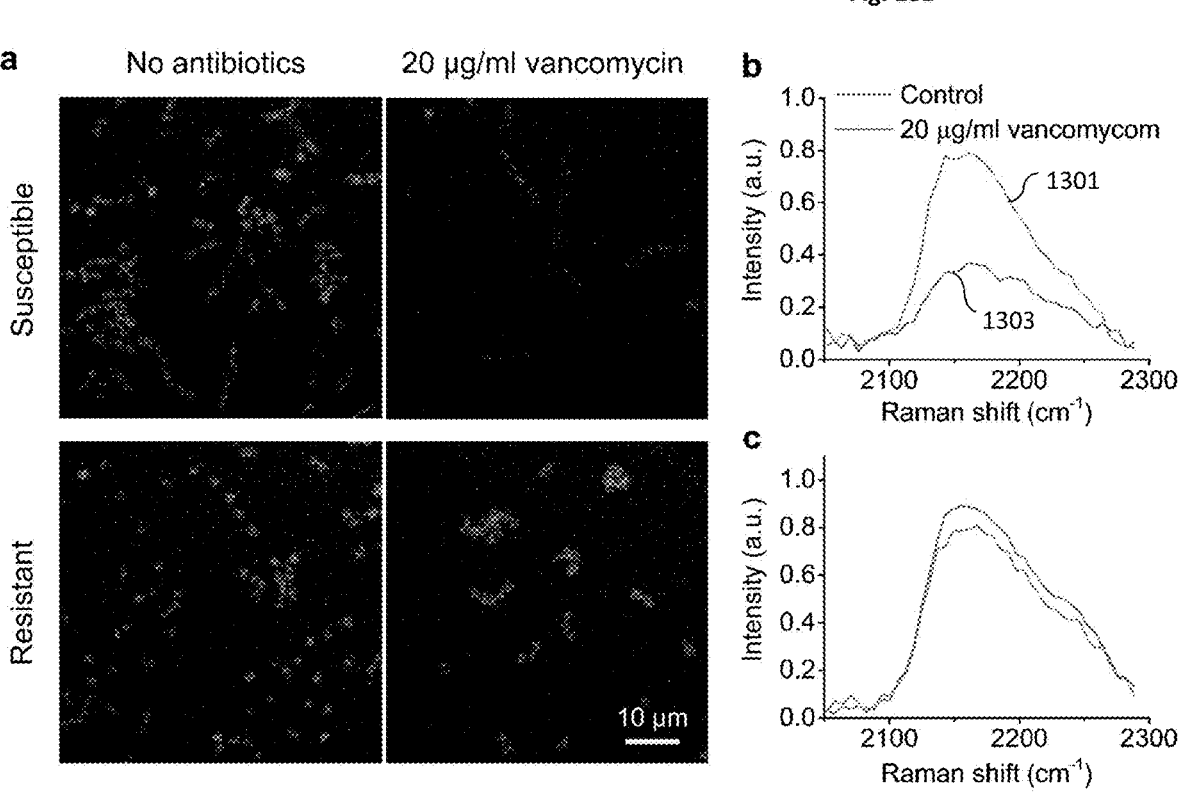
FIG. 13A shows SRS imaging at C-D vibrational region for vancomycin susceptible and resistant *E. faecalis* cultured in glucose-d7 containing medium for 3 h with and without 20 µg/ml vancomycin treatment.
FIG. 13B illustrates the corresponding spectra for vancomycin susceptible *E. faecalis* with vancomycin treatment and without vancomycin treatment data for bacteria cultured in glucose-d$_7$ containing medium for 3 hours.
FIG. 13C illustrates the corresponding spectra for vancomycin susceptible *E. faecalis* with vancomycin treatment and without vancomycin treatment data for bacteria cultured in glucose-d$_7$ containing medium for 3 hours.
Figure 14:
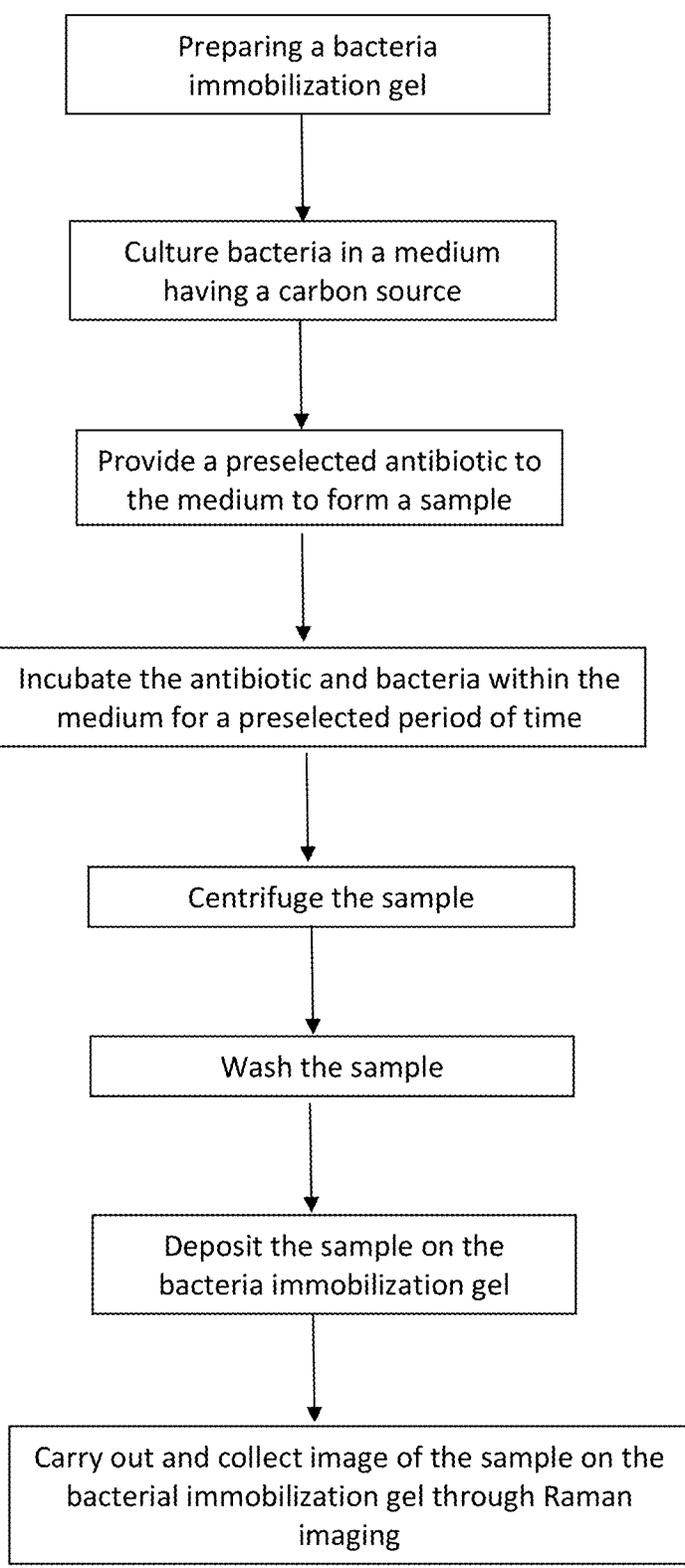
FIG. 14 depicts a method for the AST procedure, according to the present disclosure.

FIG. 6A-D depict results of C-D component change in bacteria cultured with glucose-d7 containing medium in the presence and absence of 20 μg/ml vancomycin. FIGS. 6A and 6B show the temporal dynamics of C-D component after MCR analysis for VSE and VRE, respectively. The average intensity of C-D component in individual bacteria was quantified and plotted in FIGS. 6C and 6D for VSE and VRE, respectively. For VSE in control without vancomycin treatment, bacteria cultured in glucose-d$_7$ medium for about 0.5 and 1 h has similar intensity of C-D component, while the intensity of C-D component for 3 h is higher (FIG. 6C), indicating slightly increased glucose-d$_7$ uptake with time. For VRE in control, the C-D component in individual comycin treatment 1301. FIG. 13C illustrates the corresponding spectra for vancomycin susceptible *E. faecalis* with and without vancomycin treatment that illustrates no shift in the imaging data.

Additional test were done to determine if the metabolic imaging based AST method works for other antibiotics. VSE *E. faecalis* 31970 was cultivated in glucose-d$_7$ containing M9 medium with 5 different antibiotics, vancomycin, linezolid, daptomycin, gentamycin and erythromycin. These antibiotics are commonly prescribed in clinics for bacterial infection treatment, and have different mechanisms of action. FIG. 10A-F depict the SRS imaging of VSE after 1 h cultivation in glucose-d$_7$ containing medium without (control) and with the addition of each antibiotic with a final concentration of 20 μg/mL. A significant reduction of the C-D signal was observed in bacteria treated with vancomycin and linezolid only. Therefore, it is concluded that *E. faecalis* 31970 is susceptible to vancomycin and linezolid, but resistant to daptomycin, gentamycin and erythromycin based on our metabolic imaging method. MICS of these antibiotics to VSE were determined by conventional culture based method to confirm this as shown in Table 1 below. The susceptibility of VSE to these 5 antibiotics is consistent with the results determined by our metabolic imaging method.

TABLE 1

Figures 11A, 11B, 11C, 11D:
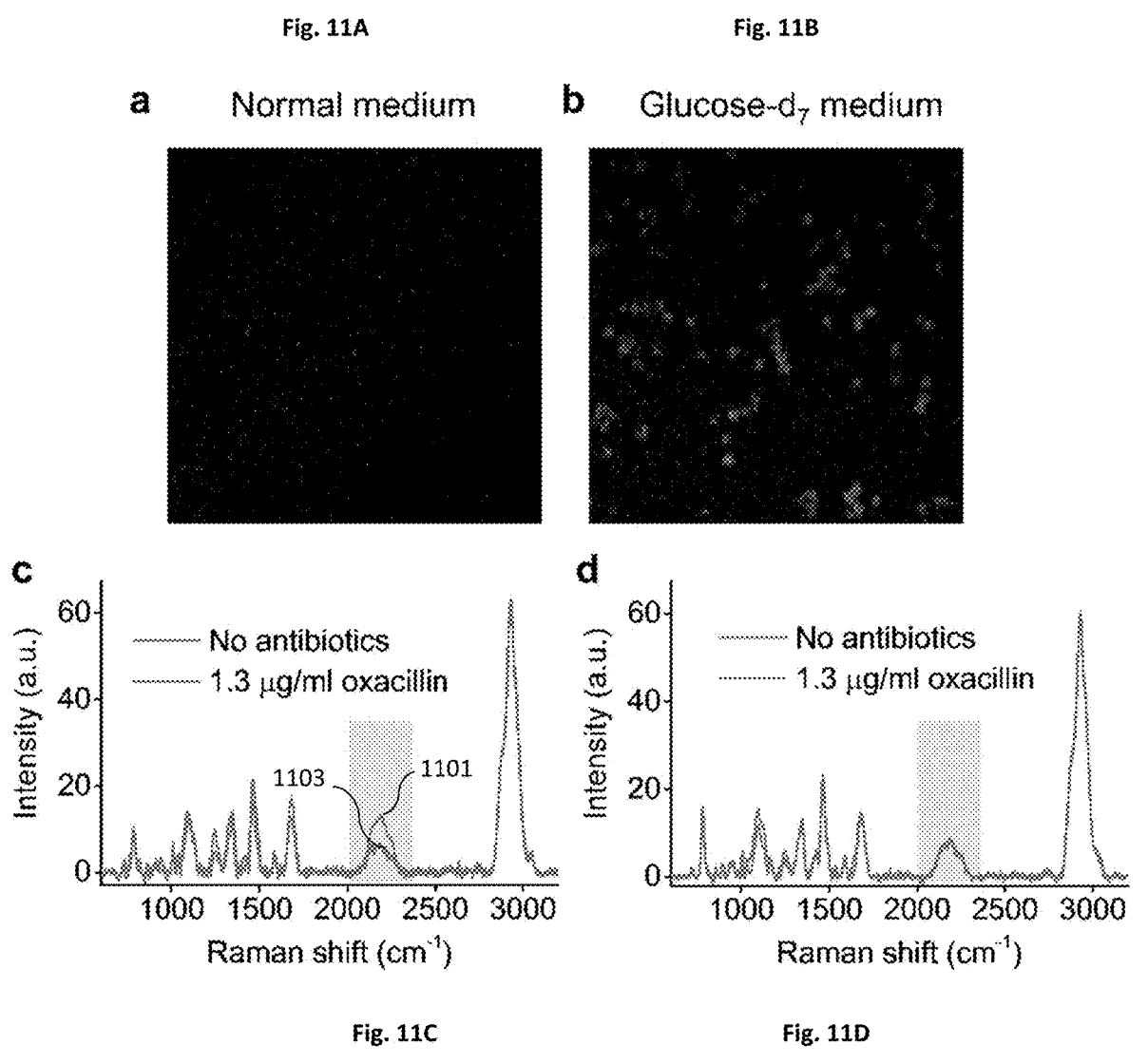
Figures 12A, 12B, 12C:
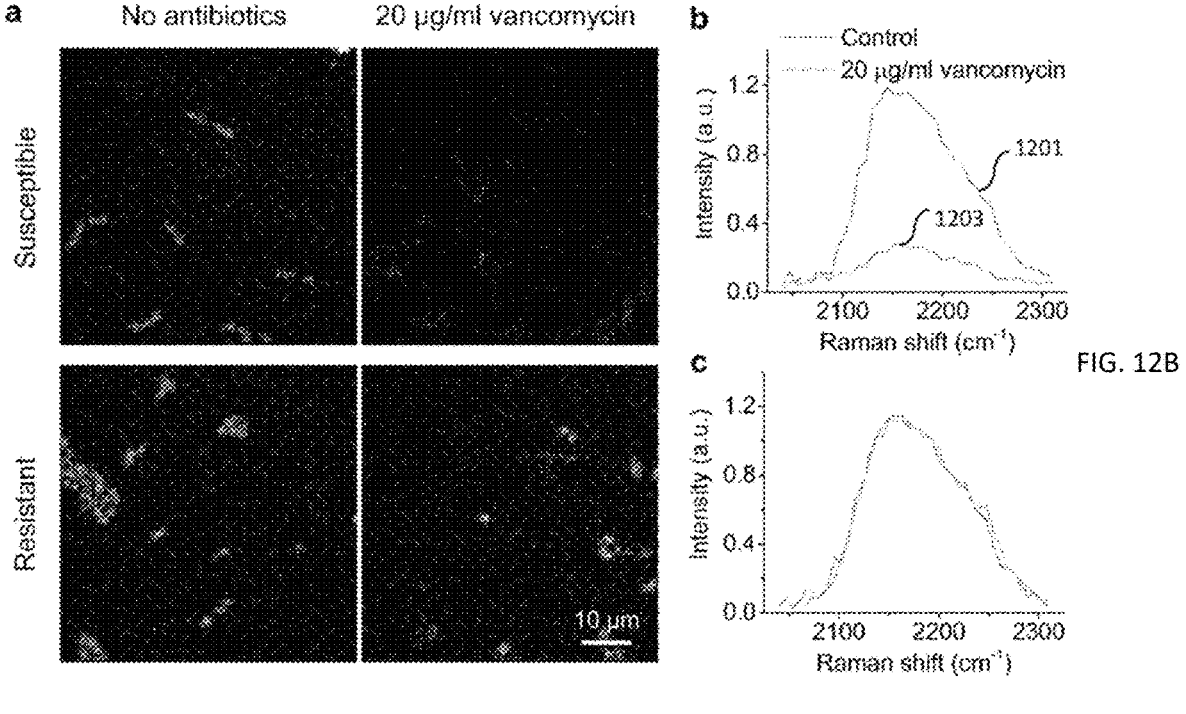
FIG. 12A shows SRS imaging at C-D vibrational region for vancomycin susceptible and resistant *E. faecalis* cultured in glucose-d7 containing medium for 1 h with and without 20 µg/ml vancomycin treatment.
FIG. 12B illustrates the corresponding spectra for vancomycin susceptible *E. faecalis* cultured in glucose-d7 containing medium for 1 h with vancomycin treatment and without vancomycin treatment.
FIG. 12C illustrates the corresponding spectra for vancomycin susceptible *E. faecalis* cultured in glucose-d7 containing medium for 1 h with and without vancomycin treatment.

| MICs (μg/mL) of antibiotics against *E. faecalis* 31970. | | | | | |
| --- | --- | --- | --- | --- | --- |
| Antibiotics | Gentamycin | Linelozid | Erythromycin | Vancomycin | Daptomycin |
| MIC(μg/mL) | >256 | 2 | >256 | 1 | 32 | bacteria has similar intensity from about 0.5 to 3 h (FIG. 6D). Vancomycin treatment significantly reduced the intensity of C-D component for VSE, student's t-test was used to analyze the significance between the control and the treated group for VSE, the p-values are 2.2×10$^{-13}$, 2.0×10$^{-11}$ and 3.9×10$^{-15}$ for about 0.5, 1 and 3 h results, respectively. Vancomycin treatment did not significantly reduce the intensity of C-D component in VRE. Interestingly, 3 h vancomycin treatment for VRE has higher intensity of C-D component than the control group (p-value is 5×10$^{-4}$), this can likely be attributed to the metabolic response of VRE to the treatment of vancomycin, whereby the cells increase the uptake of glucose to combat the antibiotics stress. The results demonstrate that vancomycin treatment significantly reduce the uptake of glucose-d$_7$ in VSE, while it does not reduce the uptake of glucose-d$_7$ in VRE over a time range of 3 h. Therefore, the susceptibility of VSE and VRE to vancomycin can be rapidly determined. FIG. 12A-C depict corresponding and imaging data for bacteria cultured in in glucose-d$_7$ containing medium for 1 h. FIG. 12A shows SRS imaging at C-D vibrational region for vancomycin susceptible and resistant *E. faecalis* cultured in glucose-d$_7$ containing medium with and without 20 μg/ml vancomycin treatment. As shown in FIG. 12B, the corresponding spectra for vancomycin susceptible *E. faecalis* with vancomycin treatment 1203 and without vancomycin treatment 1201. Additionally, FIG. 12C illustrates the corresponding spectra for vancomycin susceptible *E. faecalis* with and without vancomycin treatment that illustrates no shift in the imaging data. Similarly, FIGS. 13A-C respectively depict corresponding and imaging data for bacteria cultured in glucose-d$_7$ containing medium for 3 h. FIG. 13B illustrates the corresponding spectra for vancomycin susceptible *E. faecalis* with vancomycin treatment 1303 and without van- To verify that the method works for other bacteria species, *S. aureus* was tested using one strain susceptible (MIC 0.0625 μg/ml) and one strain resistant to oxacillin. The metabolic activity of glucose-d$_2$ can be observed in single bacterium cultivated in glucose-d$_2$ containing medium for 0.5 h by SRS imaging (FIG. 11B). When bacteria were treated with 1.3 μg/ml oxacillin for 0.5 h, a reduction in C-D peak was observed for susceptible strain 1103 compared to the control 1101 not being treated by the oxacillin (FIG. 11C) and no significant change was observed for resistant strain (FIG. 11D). Therefore, susceptible and resistant *S. aureus* can be determined in about 0.5 h.

The present disclosure further provides for a metabolic imaging method that can determine the susceptibility of live bacteria and the MICS of antibiotics within about 30 minutes by monitoring the metabolic activity of bacteria at the single cell level. This method reduces the time needed for AST from at least 16 h to 24 h for the conventional culture based method to 0.5 h. The AST at the single bacterium level based on metabolic imaging is especially useful for non-culturable or fastidious bacteria, since metabolic activity happens faster than the phenotypic growth, bacteria may not need to replicate to detect the response of metabolic activity to antibiotics treatment.

For the D$_2$O method the SRS imaging-based method was demonstrated using *P. aeruginosa* to show the metabolic activity using heavy water (D$_2$O). For the broad C-D vibrational spectrum, the signal of bacterium can be improved by more than about 5 times with femtosecond SRS without chirping compared to the chirped SRS. The D$_2$O metabolism in bacteria can respond differently and as fast as about 10 minutes to different antibiotics depending on the susceptibility of bacteria being used for SRS microscopy for metabolic activity studies in a single bacterium, and also for rapid AST that works generally to different bacteria.

Figures 15A, 15B, 15C:
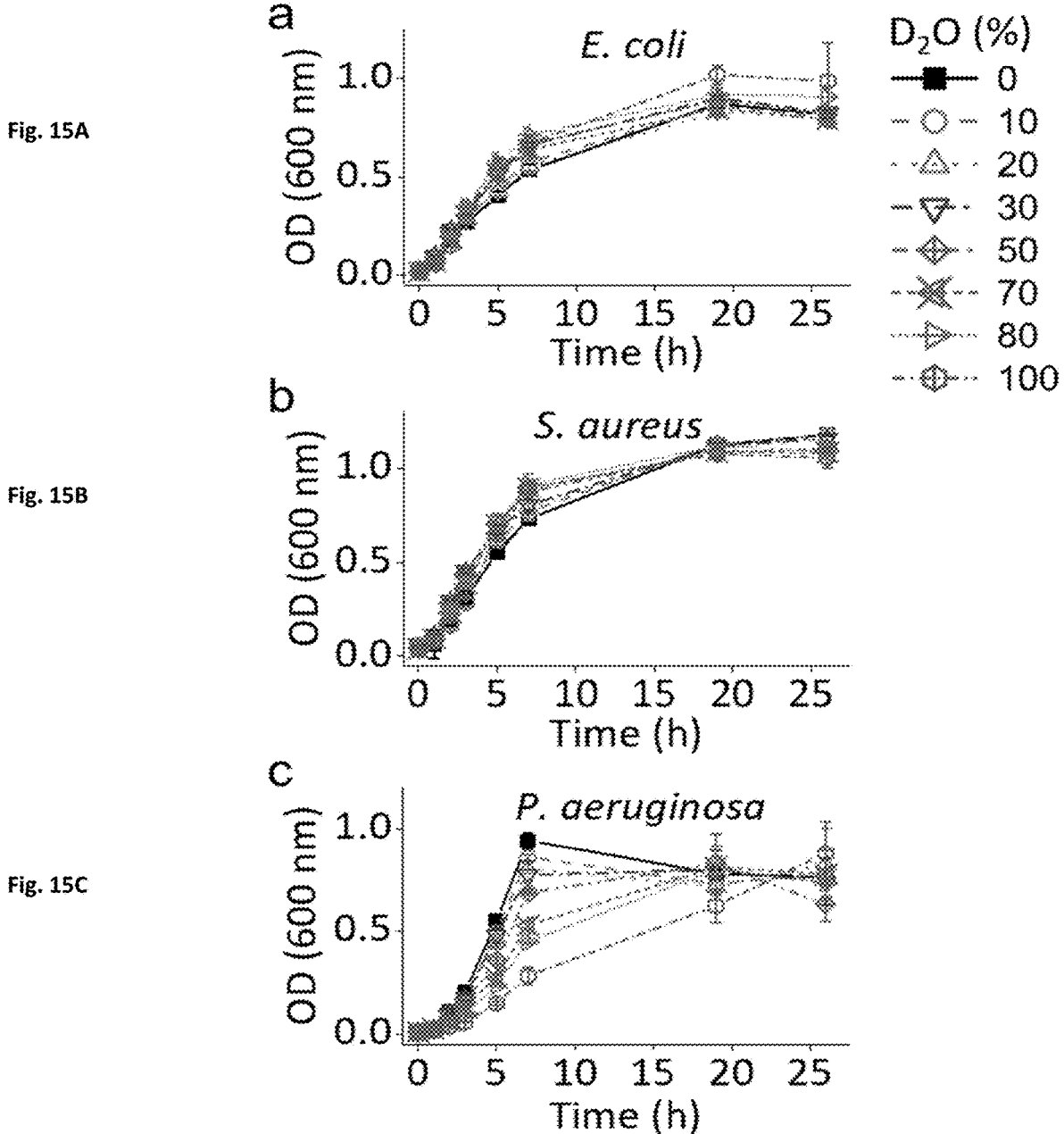
FIG. 15A is a graph of optical density (OD) measurement at about 600 nm for *E. coli* grown in a D$_2$O containing medium.
FIG. 15B is a graph of optical density (OD) measurement at about 600 nm for *S. aureus* grown in a D$_2$O containing medium.
FIG. 15C is a graph of optical density (OD) measurement at about 600 nm for *P. aeruginosa* grown in a D$_2$O containing medium.

The toxicity of $D_2O$ was first tested on bacteria by measuring the growth in a $D_2O$ containing medium. Three types of bacteria (*E. coli*, *S. aureus*, and *P. aeruginosa*) were cultured at different concentrated $D_2O$ containing LB medium, and their growth were monitored with optical density (OD) measurement at about 600 nm. A $D_2O$ concentration up to 100% did not show significant toxicity to the growth of *E. coli* and *S. aureus*, as indicated by the growth curve in $D_2O$ media of various concentrations (FIGS. 15A-B). The growth of *P. aeruginosa* was initially slowed down in LB medium with $D_2O$ concentration of 70% and up, but eventually restored to normal growth after about 18 hours for $D_2O$ concentration of 70% and 80%, and about 22 hours for $D_2O$ concentration of 100% (FIG. 15c). Therefore, $D_2O$ in the medium does not induce significant toxicity to the bacteria.

Figures 16A, 16B, 16C:
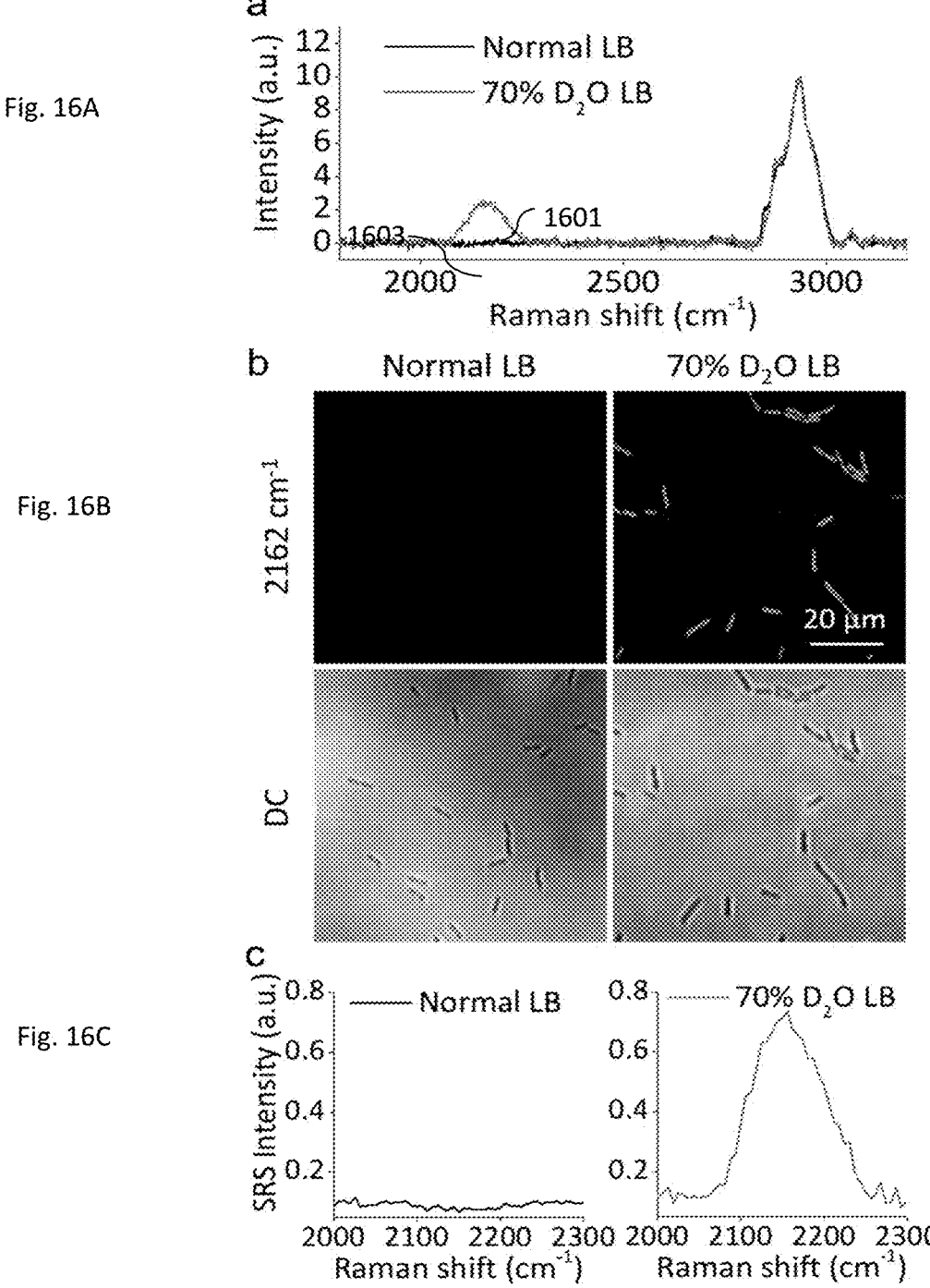
FIG. 16A is spontaneous Raman spectra of high-density bacteria cultivated in the D$_2$O containing medium and normal medium.
FIG. 16B is imaging for bacterium cultivated in normal medium and D$_2$O containing medium.
FIG. 16C depicts results of Corresponding SRS spectra of single bacterium in FIG. 16B.

A 70% $D_2O$ containing LB medium was provided to cultivate bacteria, and used *P. aeruginosa* as a model to test whether the $D_2O$ metabolic activity in single bacterium can be monitored by SRS microscope. *P. aeruginosa* was separately cultivated in normal LB and 70% $D_2O$ containing LB medium for about 2 hours, and then centrifuged and washed in water to remove the culture medium. Referring to FIG. 16A, Spontaneous Raman spectra of high-density bacteria showed a broad peak 1601 between about 2070 to about 2250 cm−1 at C-D vibrational region for bacteria cultivated in the $D_2O$ containing medium), indicating $D_2O$ had been successful utilized for biomolecule synthesis. For control, bacteria cultivated in normal medium 1603 did not have this peak at this region (FIG. 16A). To image single bacterium, bacteria were further diluted and deposited on an agarose gel pad. By tuning the SRS frequency to C-D region at about 2162 cm−1, a strong signal was observed for individual bacterium cultivated in $D_2O$ containing medium (FIG. 16B, right). As a control, no C-D signal was observed for bacteria cultured in normal medium (FIG. 16B, left). The results were confirmed by SRS spectrum (FIG. 16C) obtained through temporal tuning of chirped pump and Stokes femtosecond pulses.

To further improve the C-D signal of single bacterium, non-chirped femtosecond pulses were tested to improve the signal-to-noise (SNR) ratio over the chirped picosecond pulses. Because the C-D vibration band is relatively broad with a width of about 180 cm−1 (FIG. 16C), the femtosecond SRS without chirping may further increase the SNR. To test this, we cultivated *P. aeruginosa* in 70% $D_2O$ containing LB medium for about 30 minutes, and imaged them at about 2162 cm−1 by chirped picosecond pulses and non-chirped femtosecond pulses, respectively illustrated in FIGS. 17A and 17C. The pump and Stokes power were adjusted to make sure the same average pump and Stokes power were used at the sample. The SNR of individual bacterium with picosecond and femtosecond SRS was 1.43 and 7.81, respectively, indicating about 5.46 times SNR improvement with femtosecond SRS over picosecond SRS shown in FIGS. 17B and 17D respectively. This improvement can attributed to two different aspects of the setup, one is that the C-D vibrational band is broad, and the femtosecond SRS can detect broader band signal than the chirped picosecond SRS. Secondly, the pulse being chirped can reduce the peak power of the pulses. Although the same average power was used at the sample, the reduced peak power decreased SNR significantly due to the nonlinear effect of SRS.

A time lapse of $D_2O$ metabolic activity can be carried out in single *P. aeruginosa* with femtosecond SRS imaging. *P.*

Figures 18A, 18B, 18C, 18D, 18E:
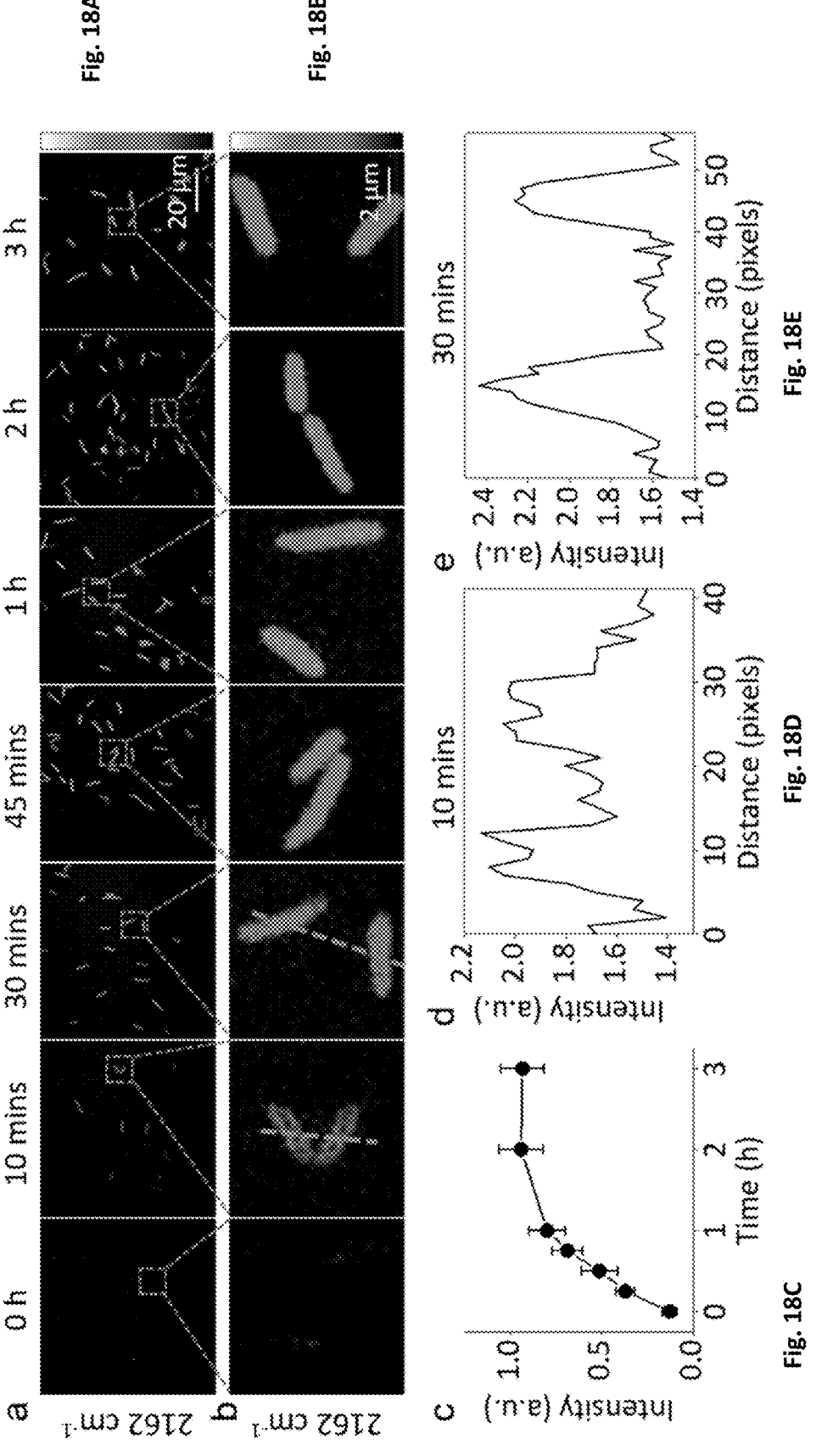
FIG. 18A depicts results of a time lapse of $D_2O$ biosynthesis in *P. aeruginosa* using C-D SRS imaging of *P. aeruginosa* cultivated in 70% $D_2O$ containing LB medium from time 0 to 3 hours.
FIG. 18B is a magnified image of individual *P. aeruginosa* in the rectangular square from FIG. 18B.
FIG. 18C is a graphical illustration of the dynamics of average SRS intensity of individual *P. aeruginosa* from FIG. 18A, wherein the error bars indicate standard deviation (N>10).
FIG. 18D is an Intensity plot of the dashed line over bacteria from the 10 minutes result in FIG. 18B.
FIG. 18E is an intensity plot of the dashed line over bacteria from the 30 minutes result in FIG. 18B.

*aeruginosa* was first cultivated in about 70% $D_2O$ containing LB medium for up to about 3 hours, at different time points, about 500 μl bacteria were centrifuged, washed and deposited on agarose gel pad for imaging. FIG. 18A shows the SRS imaging of single *P. aeruginosa* at about 2162 cm−1, C-D signal in individual *P. aeruginosa* can be observed after as short as about 10 minutes. Statistical analysis showed that the average C-D signal intensity in individual bacterium increase with time, and saturate at ~1.5 hours as shown in FIG. 18C, which is about three generations since the generation time of *P. aeruginosa* cultivated in LB medium is 24-27 minutes. To view individual bacterium more clearly, the images in FIG. 18A were further zoomed in in FIG. 18B. Interestingly, FIG. 18B shows the 10 minute result, a stronger signal was observed in the cell periphery of bacterium, as indicated by the intensity plot over the bacteria shown in FIG. 18D. In contrast, in and after 30 minutes, FIG. 17B shows the signal intensity is stronger in bacteria cell center, as indicated by the intensity plot over bacteria in the 30 minutes result shown in FIG. 18E. Collectively, these results suggest that water is initially used to synthesize cell membrane and/or cell wall in *P. aeruginosa*.

Figures 19A, 19B:
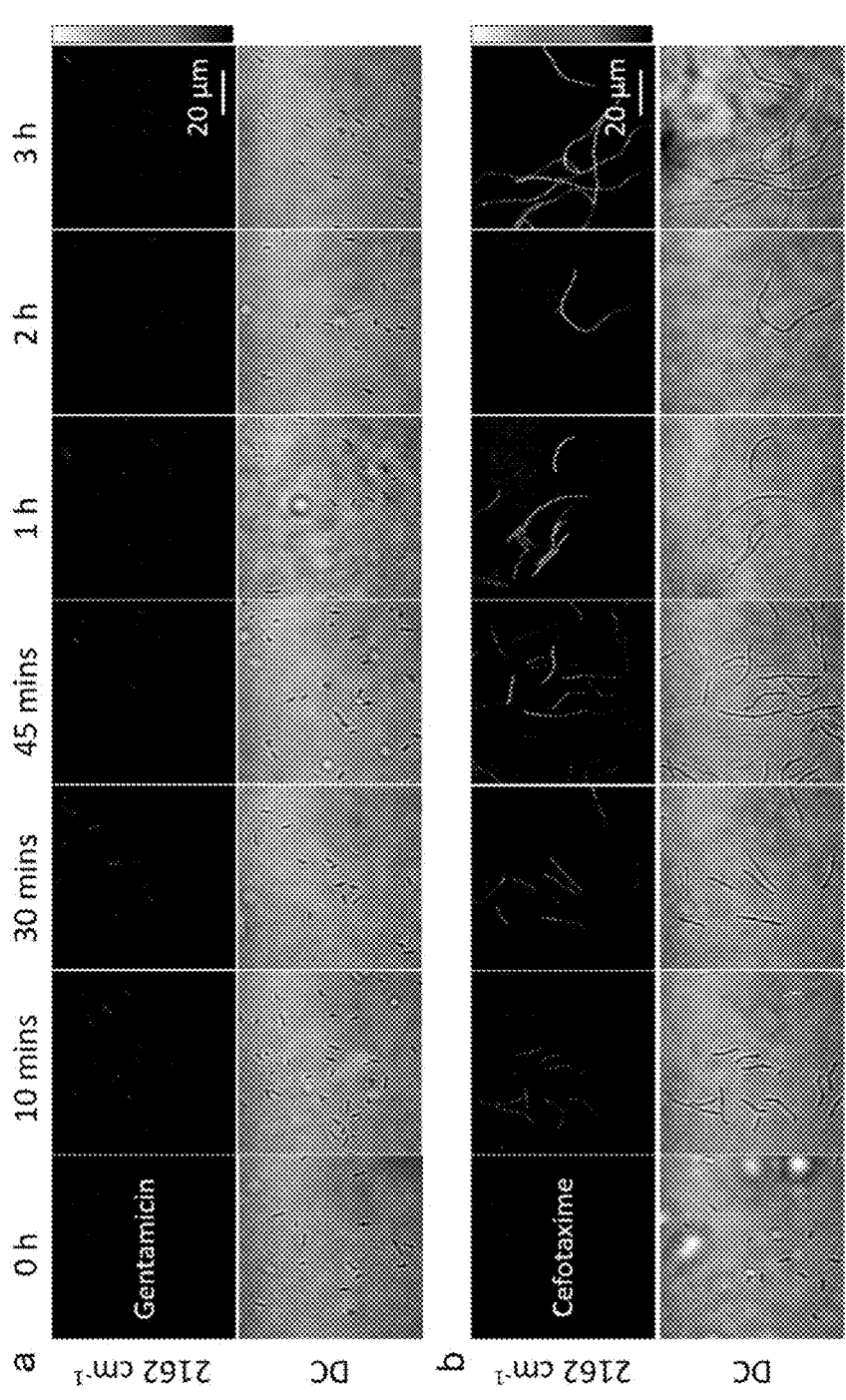
FIG. 19A depicts results of C-D SRS imaging at 2162 $cm^{-1}$ and transmission imaging of *P. aeruginosa* cultivated in 70% $D_2O$ containing LB medium with the addition of 20 μg/ml gentamicin.
FIG. 19B depicts results of C-D SRS imaging at 2162 $cm^{-1}$ and transmission imaging of *P. aeruginosa* cultivated in 70% $D_2O$ containing LB medium with the addition of 20 μg/ml cefotaxime.

*P. aeruginosa* were cultivated in 70% $D_2O$ containing LB medium, with the addition of 20 μg/ml gentamicin or cefotaxime to determine the antibiotic effect on the metabolic activity of $D_2O$ in bacteria, and wherein it is suitable for use of rapid AST with SRS imaging. The susceptibility of *P. aeruginosa* were pre-determined to be susceptible to gentamicin and resistant to cefotaxime at this concentration using conventional culture-based microdilution method. SRS imaging at about 2162 cm−1 showed that the C-D signal was significantly reduced after cultivation in 20 μg/ml gentamicin shown in FIG. 19A, indicating that the metabolic activity of $D_2O$ in *P. aeruginosa* was inhibited by gentamicin. On contrary, *P. aeruginosa* cultivated in cefotaxime can be observed at about 2162 cm−1 SRS imaging at all time points, indicating active metabolic activity of $D_2O$ in *P. aeruginosa* when cultivated in cefotaxime. We observed that *P. aeruginosa* tends to form long rods when cultivated in cefotaxime as shown in FIG. 19B, this can be due to cefotaxime is β-lactam antibiotics, which inhibit the synthesis of bacterial cell wall, therefore *P. aeruginosa* can still grow, but cannot divide when cultivated in cefotaxime. This filamentary formation may also be observed when *P. aeruginosa* was treated with other β-lactam antibiotics 10.

The $D_2O$ metabolic activity of bacteria can be used to rapid differentiate the antibiotic susceptibility of bacteria and examined using the average C-D signal intensity of bacteria being compared between three groups shown in FIGS. 19C-H, the control without antibiotics treatment (FIG. 18A), treated with gentamicin (FIG. 19A), and treated with cefotaxime (FIG. 19B). To separate the susceptible and resistant group, we determined an about 65% line threshold, which is about 65% the average C-D intensity of bacteria in control, in all plots from about 10 minutes to about 3 hours results shown in FIGS. 19C-H. This threshold can clearly divide the susceptible and resistant groups, the group treated with gentamicin was always below the threshold, and the group treated with cefotaxime was always above the threshold, at all time points. Therefore, the susceptibility of *P. aeruginosa* to gentamicin and cefotaxime can be determined in as short as about 10 minutes.

The SRS metabolic imaging method can determine the minimal inhibitory concentration (MIC) of antibiotics to bacteria and was done by cultivating *P. aeruginosa* in about 70% $D_2O$ containing LB medium for about 1 hour with the addition of gentamicin with serial diluted concentration. As shown in FIG. 20A, SRS imaging at 2162 cm−1 showed that the $D_2O$ metabolic activity of *P. aeruginosa* was inhibited at 8 μg/ml or higher concentrated gentamicin cultivation. For control, no C-D signal was observed for *P. aeruginosa* cultivated in normal LB medium. The average intensity of *P. aeruginosa* C-D signal was plotted and compared as shown in FIG. 20B. With the 65% intensity threshold, the MIC was determined to be about 8 μg/ml with SRS-based $D_2O$ metabolic imaging method, which is consistent to the result determined by the conventional culture-based method.

Numerous and varied other arrangements can be readily devised by those skilled in the art without departing from the spirit and scope of the invention. Moreover, all statements herein reciting principles, aspects and embodiments of the present invention, as well as specific examples thereof, are intended to encompass both structural and functional equivalents thereof. Additionally, it is intended that such equivalents include both currently known equivalents as well as equivalents developed in the future, i.e. any elements developed that perform the same function, regardless of structure. All references cited herein are incorporated by reference. Additional disclosure is found in Appendix A, the entirety of which is incorporated herein by reference.

What is claimed is:

1. A hyperspectral stimulated Raman scattering imaging apparatus for collecting images for antibiotic susceptibility testing, the apparatus comprising:
   a dual output femtosecond pulse laser, the dual out femtosecond pulse layer including:
   a pump beam;
   a Stokes beam;
   the Stoke beam path modulated by an acousto-optical modulator; the pump beam path having a translational stage to tune a delay between the pump beam and the Stokes beam;
   a combiner, the combiner adapted to combine the pump beam and the Stokes beam;
   a laser scanning microscope, the laser scanning microscope having an objective adapted to focus the pump beam and the Stokes beam on a sample, and an oil condenser, the oil condenser adapted to collect the laser from the sample;
   a filter, the filter positioned after the condenser and adapted to filter out the Stokes beam;
   a photodiode, the photodiode positioned after the filter, the photodiode detecting the pump beam; and
   a lock in amplifier, the lock in amplifier adapted to extract the pump beam signal loss.

2. The imaging apparatus as in claim 1, further comprising a chirping device, the chirping device adapted to form a different pulse duration between the Stoke beam and the pump beam.

3. The imaging apparatus as in claim 2, wherein the chirping device are SF57 glass rods.

4. The imaging apparatus as in claim 3, wherein a pair of filters are used.

5. The imaging apparatus as in claim 1, wherein the laser scanning microscope objective is a 60× water objective.

6. The imaging apparatus of claim 2, wherein the pulse duration of the pump beam is between 1.5 and 2 ps and the pulse duration for the Stokes beam is between 1.0 and 1.4 ps.

7. The imaging apparatus of claim 2 wherein the chirping devices is adapted to form a pulse duration of 1.9 ps for the pump beam and 1.3 ps for the Stokes beam.

8. The imaging apparatus of claim 1 wherein the pump beam is a 120-fs tunable laser and having a pump beam path and the Stokes beam is a 220 fs laser centered at 1040 nm having a Stokes beam path.

9. The imaging apparatus of claim 1, wherein the sample is generated by cultivating the bacteria in a medium having a nutrient source;
   adding a preselected antibiotic having a pre-selected concentration to the medium to form a sample;
   incubating the sample within the medium for a preselected period of time;
   centrifuging the sample;
   washing the sample;
   depositing the sample on a bacteria immobilization gel;
   imaging the sample on the bacteria immobilization gel, using coherent Raman microscopy.

10. The imaging apparatus of claim 9, wherein the stimulate Raman scattering system uses a pump beam and a Stokes beam, wherein both beams are chirped with one or more glass rods, thereby creating a pulse duration of between 1-2 ps for both the pump beam and Stokes beam.

11. The imaging apparatus of claim 9, wherein the sample image is collected though hyperspectral coherent Raman microscopy.

12. The imaging apparatus of claim 9, wherein the sample image is collected through single frequency coherent Raman microscopy.

13. The imaging apparatus of claim 9, wherein the immobilization gel is comprised of an agarose gel.

14. The imaging apparatus of claim 9, wherein the nutrient source has a carbon source is solely composed from between 0.1-10% glucose-d7.

15. The imaging apparatus of claim 9, wherein the nutrient source is composed from a medium having deuterium dioxide.

16. The imaging apparatus of claim 9, wherein the carbon source is composed of a combination of both glucose-d7 and deuterium dioxide.

17. The imaging apparatus of claim 9, wherein the Raman imaging can be stimulated Raman scattering imaging, coherent anti-Stokes Raman scattering imaging, or coherent Raman induced Kerr effect imaging.

* * * * *